(12) United States Patent
Iyer et al.

(10) Patent No.: US 11,813,470 B2
(45) Date of Patent: *Nov. 14, 2023

(54) MULTI-AXIS COIL FOR IMPLANTABLE MEDICAL DEVICE

(71) Applicant: Medtronic, Inc., Minneapolis, MN (US)

(72) Inventors: Rajesh V. Iyer, Eden Prairie, MN (US); Gordon O. Munns, Stacy, MN (US); Christian S. Nielsen, River Falls, WI (US); Craig L. Schmidt, Eagan, MN (US); Paul B. Young, New Richmond, WI (US)

(73) Assignee: Medtronic, Inc., Minneapolis, MN (US)

( * ) Notice: Subject to any disclaimer, the term of this patent is extended or adjusted under 35 U.S.C. 154(b) by 451 days.

This patent is subject to a terminal disclaimer.

(21) Appl. No.: 17/027,013

(22) Filed: Sep. 21, 2020

(65) Prior Publication Data

US 2021/0001131 A1    Jan. 7, 2021

Related U.S. Application Data

(63) Continuation of application No. 16/021,059, filed on Jun. 28, 2018, now Pat. No. 10,821,292.

(51) Int. Cl.
*A61N 1/378* (2006.01)
*H02J 7/00* (2006.01)
(Continued)

(52) U.S. Cl.
CPC ....... *A61N 1/3787* (2013.01); *A61N 1/37229* (2013.01); *H01F 5/04* (2013.01);
(Continued)

(58) Field of Classification Search
CPC .............. A61N 1/3787; A61N 1/37512; A61N 1/37229; A61N 1/3756; H02J 7/0042;
(Continued)

(56) References Cited

U.S. PATENT DOCUMENTS 5,117,824 A     6/1992  Keimel et al.
5,548,218 A     8/1996  Lu
(Continued)

FOREIGN PATENT DOCUMENTS

EP           0693733 A1    1/1996
EP           3045203 A2    7/2016
(Continued)

OTHER PUBLICATIONS

U.S. Appl. No. 16/021,059, filed by Rajesh V. Iyer et al., filed Jun. 28, 2018.
(Continued)

*Primary Examiner* — Edward Tso
*Assistant Examiner* — Aaron Piggush
(74) *Attorney, Agent, or Firm* — Shumaker & Sieffert, P.A.

(57) ABSTRACT

Systems, devices and methods allow inductive recharging of a power source located within or coupled to an implantable medical device while the device is implanted in a patient. The implantable devices in some examples include a multi-axis antenna having a plurality of coil windings arranged orthogonal to one another. The multi-axis antenna configured to generate at least a minimum level of induced current for recharging a power source of the implanted medical device regardless of the orientation of a direction of a magnetic field imposed on the multi-axis antenna relative to an orientation of the implanted medical device and the multi-axis antenna for a given energy level of the imposed magnetic field.

17 Claims, 11 Drawing Sheets

(51) Int. Cl.
    *A61N 1/372*         (2006.01)
    *H01F 5/04*          (2006.01)
    *H01F 38/14*        (2006.01)
    *H01F 41/10*        (2006.01)
    *A61N 1/375*        (2006.01)
    *H01F 5/02*         (2006.01)

(52) U.S. Cl.
    CPC ............ *H01F 38/14* (2013.01); *H01F 41/10*
    (2013.01); *H02J 7/0042* (2013.01); *A61N*
    *1/3756* (2013.01); *A61N 1/37512* (2017.08);
    *H01F 5/02* (2013.01)

(58) Field of Classification Search
    CPC .... H02J 7/025; H01F 5/02; H01F 5/04; H01F 38/14; H01F 41/10
    USPC ............... 320/108, 112, 162; 607/32, 60, 61
    See application file for complete search history.

(56) References Cited

U.S. PATENT DOCUMENTS

| | | | |
|---|---|---|---|
| 6,008,622 | A | 12/1999 | Nakawatase |
| 6,459,924 | B1 | 10/2002 | Creighton, IV et al. |
| 7,474,098 | B2 | 1/2009 | King |
| 7,816,915 | B2 | 10/2010 | Susel et al. |
| 7,924,000 | B2 | 4/2011 | Susel et al. |
| 8,175,716 | B2 | 5/2012 | Rahman et al. |
| 8,612,014 | B2 | 12/2013 | Rahman et al. |
| 8,634,928 | B1 | 1/2014 | O'Driscoll et al. |
| 9,318,780 | B2 | 4/2016 | Robertson et al. |
| 9,620,985 | B2 | 4/2017 | Rosenfeld |
| 9,711,272 | B2 | 7/2017 | Hassan-Ali et al. |
| 10,821,292 | B2* | 11/2020 | Iyer ...................... A61N 1/3756 |
| 2002/0177884 | A1 | 11/2002 | Ahn et al. |
| 2004/0135579 | A1 | 7/2004 | Takizawa et al. |
| 2008/0027513 | A1 | 1/2008 | Carbunaru et al. |
| 2010/0201315 | A1 | 8/2010 | Oshimi et al. |
| 2011/0257703 | A1 | 10/2011 | Kerber et al. |
| 2011/0295340 | A1 | 12/2011 | Rahman et al. |
| 2011/0301668 | A1 | 12/2011 | Forsell |
| 2012/0248883 | A1 | 10/2012 | Konanur et al. |
| 2013/0024059 | A1 | 1/2013 | Miller et al. |
| 2013/0043734 | A1 | 2/2013 | Stone et al. |
| 2013/0223028 | A1 | 8/2013 | Arne et al. |
| 2013/0241300 | A1 | 9/2013 | Miyamoto |
| 2013/0241302 | A1 | 9/2013 | Miyamoto et al. |
| 2013/0285466 | A1 | 10/2013 | Wissenwasser et al. |
| 2014/0028109 | A1 | 1/2014 | Simon et al. |
| 2014/0094674 | A1 | 4/2014 | Nurmikko et al. |
| 2014/0243848 | A1 | 8/2014 | Auricchio et al. |
| 2014/0265620 | A1 | 9/2014 | Hoarau et al. |
| 2014/0346886 | A1 | 11/2014 | Yang et al. |
| 2015/0321012 | A1 | 11/2015 | Cinbis et al. |
| 2016/0022142 | A1 | 1/2016 | Bradshaw |
| 2016/0111208 | A1 | 4/2016 | Park et al. |
| 2016/0111913 | A1 | 4/2016 | Robertson et al. |
| 2016/0131725 | A1 | 5/2016 | Sambrandamurthy et al. |
| 2016/0141097 | A1 | 5/2016 | Oo et al. |
| 2016/0189848 | A1 | 6/2016 | Nam |
| 2017/0001003 | A1* | 1/2017 | Pivonka ............... A61B 5/6871 |
| 2017/0025888 | A1 | 1/2017 | Cinbis et al. |
| 2017/0047636 | A1 | 2/2017 | Lee et al. |
| 2017/0202467 | A1 | 7/2017 | Zitnik et al. |
| 2017/0203109 | A1 | 7/2017 | Maile et al. |
| 2017/0281955 | A1 | 10/2017 | Maile et al. |
| 2018/0140850 | A1* | 5/2018 | Linder ................... H02J 50/12 |
| 2018/0140851 | A1 | 5/2018 | Maile et al. |
| 2018/0140852 | A1 | 5/2018 | Linder et al. |
| 2018/0140853 | A1 | 5/2018 | Maile et al. |
| 2018/0141444 | A1 | 5/2018 | Lee et al. |
| 2019/0199132 | A1 | 6/2019 | Ota et al. |
| 2020/0001094 | A1 | 1/2020 | Iyer et al. |
| 2020/0001095 | A1 | 1/2020 | Iyer et al. |
| 2020/0005988 | A1 | 1/2020 | Iyer et al. |
| 2020/0101291 | A1* | 4/2020 | Yakovlev ............... A61N 2/006 |
| 2020/0306528 | A1* | 10/2020 | Linden ............... A61N 1/36114 |

FOREIGN PATENT DOCUMENTS

| | | |
|---|---|---|
| WO | 0197908 A2 | 12/2001 |
| WO | 2018102435 A1 | 6/2018 |

OTHER PUBLICATIONS

Final Office Action from U.S. Appl. No. 16/021,067, dated Nov. 17, 2020, 22 pp.
Final Office Action from U.S. Appl. No. 16/021,075, dated Nov. 19, 2020, 21 pp.
De Troye et al., "The Calculation and Measurement of Helmholtz Coil Fields," Army Research Laboratory, Nov. 1994, 20 pp.
Jia et al., "The optimization of wireless power transmission: design and realization," The International Journal of Medical Robotics and Computer Assisted Surgery, Feb. 2012, pp. 337-347.
Lenaerts et al., "Inductive powering of a freely moving system," Sensors and Actuators, A 123-124, Jan. 2005, pp. 522-530.
Maile PhD, et al., "Wireless Power Transfer for Deeply Implanted Medical Devices (IMD)," Boston Scientific, presented Dec. 5-7, 2016 at Biological & Chemical Sensors Summit, San Diego, CA, 20 slides.
Tang et al., "A Low-Operating-Voltage Wireless Intermediate-Range Scheme for Energy and Signal Transmission by Magnet Coupling for Implantable Devices," IEEE Journal of Emerging and Selected Topics in Power Electronics, vol. 3, No. 1, Mar. 2015, pp. 242-251.
Von Novak, "Power Systems for Medical Implants," Qualcomm Technologies, Inc., presented Dec. 5-7, 2016 at Biological & Chemical Sensors Summit, San Diego, CA, 24 slides.
Wilken-Resman, et al., "Power Transfer Prediction Tool for Medical Implants," Qualcomm Technologies, presented Dec. 5-7, 2016 at Biological & Chemical Sensors Summit, San Diego, CA, 15 slides.
Yates, "Wireless power delivery for ventricular assist devices," Imperial College, London, Dec. 7, 2017, presented Dec. 5-7, 2017 at Biological & Chemical Sensors Summit, San Diego, CA, 40 slides.
Inernational Search Report and Written Opinion of International Application No. PCT/US2019/039681, dated Nov. 6, 2019, 11 pp.
Prosecution History from U.S. Appl. No. 16/021,059, dated Apr. 3, 2020 through Jul. 1, 2020, 51 pp.
Prosecution History from U.S. Appl. No. 16/021,067, dated Jun. 11, 2020 through Sep. 3, 2020, 16 pp.
Prosecution History from U.S. Appl. No. 16/021,075, dated Jun. 11, 2020 through Sep. 3, 2020, 35 pp.
Notice of Allowance from U.S. Appl. No. 16/021,067, dated Mar. 9, 2021, 9 pp.
Notice of Allowance from U.S. Appl. No. 16/021,075, dated Mar. 10, 2021, 9 pp.
Response to Final Office Action dated Nov. 17, 2020, from U.S. Appl. No. 16/021,067, filed Jan. 15, 2021, 20 pp.
Advisory Action dated Jan. 29, 2021, from U.S. Appl. No. 16/021,067, 4 pp.
Response to Final Office Action dated Nov. 19, 2020, from U.S. Appl. No. 16/021,075, filed Jan. 15, 2021, 18 pp.
Advisory Action dated Jan. 29, 2021, from U.S. Appl. No. 16/021,075, 4 pp.
Prosecution History from U.S. Appl. No. 16/021,059 dated Apr. 3, 2020 through Sep. 30, 2020, 53 pp.

\* cited by examiner

MULTI-AXIS COIL FOR IMPLANTABLE MEDICAL DEVICE

This application is a continuation of U.S. patent application Ser. No. 16/021,059, filed Jun. 28, 2018, the entire content of which is incorporated herein by reference.

TECHNICAL FIELD

The disclosure relates to devices and systems used to recharge a power source located within a medical device that has been implanted in a patient.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device housing. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart with or without the need for external leads, have been proposed, built, and adapted to provide both pacing and other electrical therapy to the patient.

SUMMARY

The disclosure describes implantable medical devices, systems, and associated techniques, structures, and assemblies configured to provide recharging of power sources located within medical devices that have been implanted within a patient. The implanted medical devices including these power sources that are to be recharged are often small devices that have been implanted relatively deeply within the patient, for example implanted internally within the heart of a patient. An example of such a device is the Medtronic® Micra™ self-contained pacemaker that is designed to be implanted internally, for example within a chamber of the heart of a patient, and in various examples requires no external leads coupled to the device in order to provide pacing and electrical stimulation to the heart.

The implanted devices may include a multi-axis receive antenna comprising of one or more coils coupled to recharging circuitry and configured to have currents induced into one or more of the coils to provide a recharging current for recharging a power source of the implanted medical device. Examples of multi-axis antennas as described herein provide a compact and efficient receive antenna that may be located within a housing of an implantable medical device, including versions of miniaturized implantable medical devices such as the Medtronic® Micra™ self-contained pacemaker. In some examples, the multi-axis antenna includes an antenna core formed from a ferrite material, which may have a cubic shape, with a first coil, a second coil, and a third coil, each coil having a normal axis of orientation that is orthogonal to the normal axis of each of the other coils, and formed to encircle a portion of the antenna core. Additional circuitry that includes individual diodes coupled to each coil may be arranged to rectify and to sum together the current or currents induced into the one or more of the coils in order to provide a recharging current that may be applied to a power source of the implanted medical device. The recharging current may be utilized to recharge the power source, and/or to power the operation of the implanted medical device.

When there is a need to recharge these implantable medical devices, the device including the multi-axis antenna may be placed within a magnetic field (or within a resultant magnetic field formed by a plurality of magnetic fields), which is generated by an externally powered device and one or more recharging coils so that the magnetic field (or the resultant magnetic field) is imposed onto the multi-axis antenna of the implanted medical device being recharged. The magnetic field imposed on the multi-axis antenna is arranged to induce electrical current into one or more of the coils of the multi-axis antenna. The induced electrical current or currents may be used to recharge a power source of the implanted medical device and/or to provide the electrical power used to directly operate the device. Examples of the multi-axis antenna as described in this disclosure may provide at least a minimum level of recharging current induced into the one or more coils of multi-axis antenna for a given energy level of the magnetic field imposed on the multi-axis antenna regardless of the orientation of a direction of the magnetic field relative to the orientation of the device and the multi-axis antenna.

The multi-axis antenna may have an ability to induce currents for recharging purposes irrespective of the orientation of the direction of the magnetic field relative to the orientation of the device and the multi-axis antenna, which may allow for recharging the implanted medical device using a simplified recharging system. In some examples, recharging of the implanted medical device may be accomplished using only a single planar recharging coil generating the magnetic field, or for example using just a single pair of recharging coils, to achieve rapid recharge of the implanted medical device without the need for elaborate orientation procedures and/or complex orientation equipment.

Examples described in this disclosure are directed to a method for recharging a power source located in an implanted medical device implanted in a patient, the method comprising receiving, at a multi-axis antenna of an implantable medical device, a magnetic field having a magnetic field direction, the magnetic field generated by at least one recharging coil, wherein the magnetic field induces one or more electrical currents in one or more of a plurality of coils forming the multi-axis antenna, the plurality of coils comprising a first coil having a first coil axis of orientation, a second coil having a second coil axis of orientation, and a third coil having a third coil axis of orientation, wherein the first coils axis of orientation and the second coil axis of orientation and the third coil axis of orientation are orthogonal to each other, wherein each of the first coil, the second coil, and the third coil encircle a portion of a ferrite core, and wherein the third coil encircles at least a portion of the first coil and the second coil, and wherein the second coil encircles at least a portion of the first coil. The method also includes summing, by recharging circuitry, the one or more electrical currents induced into the plurality of coils to form a recharging current; and applying, by the recharging circuitry, the recharging current to the power source of the implantable medical device to recharge the energy level stored in the power source.

Examples described in this disclosure also include an implantable medical device comprising a rechargeable power source coupled to one or more electrical circuits located within a housing of the implantable medical device, the rechargeable power source configured to provide electrical power to the one or more electrical circuits, and a multi-axis antenna comprising a plurality of coils encircling a ferrite core, the multi-axis antenna configured to generate a recharging current from one or more electrical currents induced into one or more of the plurality of coils when an externally generated magnetic field having a magnetic field direction is imposed onto the multi-axis antenna, the multi-axis antenna positioned within the housing of the implantable medical device and encircled by an antenna window forming a portion of the housing, the antenna window formed from a material that is radio transmissive, wherein the plurality of coils comprises a first coil having a first coil axis of orientation and formed from first electrically conductive winding, a second coil having a second coil axis of orientation and formed from a second electrically conductive winding, and a third coil having a third coil axis of orientation and formed from a third electrically conductive winding, the first coil axis of orientation, the second coil axis of orientation, and the third coil axis of orientation orthogonal to each other. The implantable medical device also includes recharging circuitry coupled to the multi-axis antenna and to the rechargeable power source, the recharging circuitry configured to receive the one or more electrical currents induced into one or more of the plurality of coils and to provide a recharging current to the rechargeable power source comprising a sum of the one or more electrical currents induced in one or more of the plurality of coils, wherein the multi-axis antenna and the recharging circuitry are configured to provide at least a minimum level of recharging current for a minimum level of power provided by the magnetic field imposed on the multi-axis antenna for any random orientation of the direction of magnetic field relative to an orientation of the implantable medical device.

Examples described in this disclosure also include a recharging system for recharging a power source located in an implanted medical device implanted in a patient, the recharging system comprising an electrical power source, at least one recharging coil coupled to the electrical power source and configured to generate a magnetic field having a magnetic field direction when electrically energized by the electrical power source, a multi-axis antenna located in the implantable medical device, the multi-axis antenna comprising a plurality of coils configured to generate a recharging current when the magnetic field generated by the at least one recharging coil is imposed onto the multi-axis antenna, wherein the plurality of coils comprises a first coil having a first coil axis of orientation, a second coil having a second coil axis of orientation orthogonal to the first coil axis of orientation, and a third coil having a third coil axis of orientating that is orthogonal to the both the first coil axis of orientation and the second coils axis of orientation, and wherein the third coil encircles at least a portion of the first coil and the second coil and the second coil encircles at least a portion of the first coil. The recharging system also includes recharging circuitry coupled to the multi-axis antenna, the recharging circuitry configured to sum one or more currents induced into one or more of the first coil, the second coil, and the third coil to generate the recharging current; and a switching device coupled to the multi-axis antenna and the power source of the implanted medical device, the switching device configured to be controlled by the recharging circuitry to couple the recharging current to the power source to recharge the electrical energy stored in the power source.

Examples described in this disclosure further include a passive implantable medical device comprising a multi-axis antenna comprising a plurality of coils encircling a ferrite core, the multi-axis antenna configured to generate an operating current from one or more electrical currents induced into one or more of the plurality of coils when an externally generated magnetic field having a magnetic field direction is imposed onto the multi-axis antenna, the multi-axis antenna positioned within the housing of the implantable medical device and encircled by an antenna window forming a portion of the housing, the antenna window formed from a material that is radio transmissive, wherein the plurality of coils comprises a first coil having a first coil axis of orientation and formed from first electrically conductive winding, a second coil having a second coil axis of orientation and formed from a second electrically conductive winding, and a third coil having a third coil axis of orientation and formed from a third electrically conductive winding, the first coil axis of orientation, the second coil axis of orientation, and the third coil axis of orientation orthogonal to each other. The passive implantable medical device also includes electrical circuitry coupled to the multi-axis antenna, the electrical circuitry configured to receive the one or more electrical currents induced into one or more of the plurality of coils and to electrically power and operate the passive implantable medical device using the operating current provided by the multi-axis antenna, the operating current comprising a sum of the one or more electrical currents induced in one or more of the plurality of coils, wherein the multi-axis antenna is configured to provide at least a minimum level of recharging current for a given level of power provided by the magnetic field imposed on the multi-axis antenna for any random orientation of the direction of magnetic field direction relative to an orientation of the implanted medical device.

Examples described in this disclosure also include a method A method comprising receiving, at a multi-axis antenna of a passive implantable medical device, a magnetic field having a magnetic field direction, the magnetic field generated by at least one recharging coil, wherein the magnetic field induces one or more electrical currents in one or more of a plurality of coils forming the multi-axis antenna, the plurality of coils comprising a first coil having a first coil axis of orientation, a second coil having a second coil axis of orientation, and a third coil having a third coil axis of orientation, wherein the first coils axis of orientation and the second coil axis of orientation and the third coil axis of orientation are orthogonal to each other, wherein each of the first coil, the second coil, and the third coil encircle a portion of a ferrite core, and wherein the third coil encircles at least a portion of the first coil and the second coil, and wherein the second coil encircles at least a portion of the first coil. The method further includes summing, by electrical circuitry, the one or more electrical currents induced into the plurality of coils to form an operating current; and applying, by the electrical circuitry, the operating current to the electrical circuitry of the passive implantable medical device to electrically power and operate the passive implantable medical device, the operating current comprising a sum of the one or more electrical currents induced in one or more of the plurality of coils, wherein the multi-axis antenna is configured to provide at least a minimum level of operating current for a minimum level of power provided by the magnetic field imposed on the multi-axis antenna for any random orientation of the direction of magnetic field direction relative to an orientation of the implanted medical device.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description and drawings, and from the claims.

Figure 1:
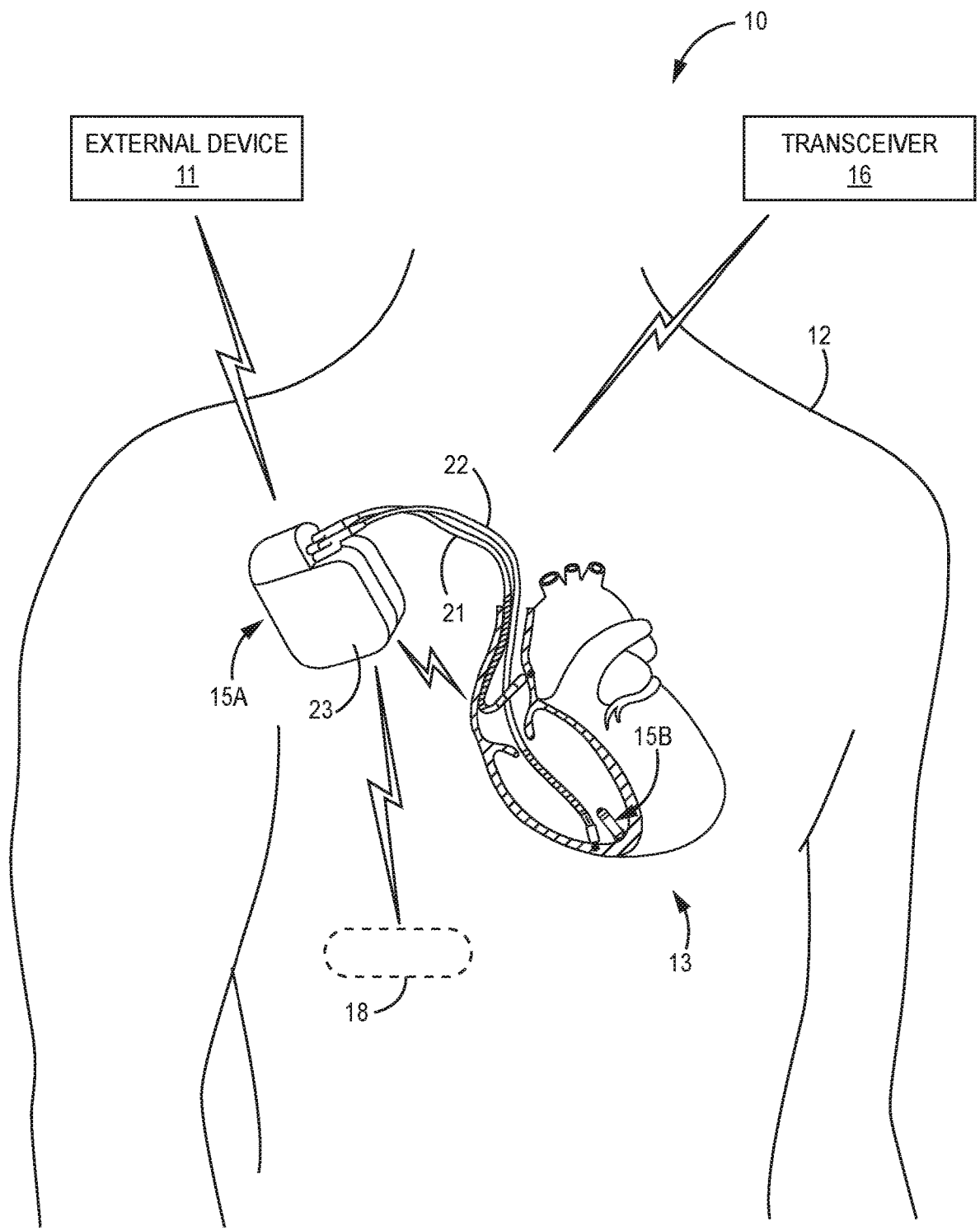
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

Traditional pacemakers, neurostimulators and implantable loop recorders may use primary batteries with finite energy as an internal power source for electrically powering operation of the device once the device has been implanted in a patient. In various examples of implanted medical devices, a primary (non-rechargeable) battery has a finite energy reservoir which limits its mission life based on its size and energy density (for a given energy usage rate). This limits the useful duration of the implanted device. Once a primary battery is exhausted, replacement of the device may be required, and although replacement of the device may be minimally invasive, it may still be traumatic to the patient. For example, risk of a pocket infection in the area of the implant may occur, which in turn may lead to longer hospital stays and increased cost burden to the patient and/or the insurance companies.

In addition, limits on the available battery energy may result in limits to therapy options for a device and/or the patient. Further, issues related to the implanted medical device may result in a need for a more energy consuming device configuration, which can further shorten the mission life of the implanted device. For example, for a percentage of patients, e.g., for twenty five percent of patients implanted with a left ventricle (LV) lead, the patient does not respond to cardiac resynchronization therapy (CRT) due to sub-optimal lead placement, resulting in the need to apply higher levels of stimulation thresholds, causing excessive battery drain and reduced longevity of the implanted device.

The use of rechargeable batteries or other rechargeable power sources that can be located within an implantable medical device and utilized to power the operation of the device is not a novel concept for overcoming the issues of limited energy primary batteries. However, use of rechargeable batteries or other rechargeable power sources may include additional technical challenges, especially if the device is implanted deep (e.g., more than three centimeters) within the body of a patient. A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to provide additional features and functions that may otherwise be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery.

In some examples, conventional inductive power transfer to implanted medical devices may be limited to devices implanted at a depth of approximately two inches or less from the surface (e.g., skin) of the patient. Fast recharge of small, deeply implanted devices such as the Medtronic® Micra™ Pacemaker via transdermal, magnetic induction when the device is implanted for example within a chamber of the heart of a patient presents many challenges. These challenges include providing an adequate magnetic field intensity and frequency at the implant location such that rapid recharge can be accomplished without exceeding electric field and magnetic field exposure safety limits for a patient, while also accounting for an uncontrolled orientation of the implanted device, and while accounting for the true spatial location of the device in addition to the device/antenna orientation.

Further, the exact orientation of the device itself following implantation of the device may be unknown, and/or may change after the implantation procedure. Thus, an implanted medical device that includes a receive antenna, such as a uni-directional or a planar antenna that may be sensitive to the alignment of the direction of imposed magnetic field with an orientation of the axis of the antenna, may require more elaborate procedures and/or more complex recharging equipment for the purpose of achieving an efficient level of inductive coupling between the magnetic field and the receive antenna. This requirement may necessitate use of more elaborate alignment procedures to align direction of the magnetic field with the orientation of the receive antenna, or may require use of more complex arrangements of multiple pairs of recharging coils in order to achieve an acceptable level of inductive coupling efficiency between the magnetic field and the receive antenna during a recharging procedure.

The devices, systems, and methods described in this disclosure address many of the challenges associated with recharging these power sources within implanted medical devices. The systems, devices, and methods described in this disclosure provide examples of a multi-axis receive antenna that may be incorporated within an implantable medical device. The multi-axis receive antenna may allow for fast recharge of a battery or other rechargeable power source within a small, deeply implanted medical device, such as the Micra™ leadless pacemaker. In some examples, the system for recharging may use a single recharging coil, or in some examples a single pair of recharging coils, to generate the magnetic field used to recharge the implanted device. The multi-axis receive antenna may be arranged to generate at least a minimum level of recharging current for a given level of power imposed by a magnetic field on the receive antenna regardless of the orientation of the magnetic field relative to an orientation of the implanted device. The use of the multi-axis receive antenna may therefore reduce or eliminate the need for a complex alignment procedure, and/or more complex arrangements of recharging coil(s) in order to achieve a minimum level of inductive coupling efficiency between the implanted medical device and the magnetic field or fields imposed on the device as part of a recharging procedure.

Thus, it is possible to establish a recharging current in the receive antenna of the implanted medical device that may be independent of the orientation of the recharging magnetic field imposed on the receive antenna, and thus provides a high level of coupling efficiency between the receive antenna and the magnetic field using just a single recharge coil, or using just a single pair of recharge coils. The systems, devices, and methods described herein provide a way to allow a magnetic field to efficiently induce electrical energy (e.g., an electrical current) into a receive antenna included within an implanted medical device with a minimum need for complex alignment and orientation between with the receive antenna and the magnetic field. The induced electrical energy may be used to recharge a power source of the implanted medical device using the externally provided magnetic field, and/or to power electronic circuitry included within or coupled to the implanted medical device, including devices that may be considered deeply implanted within the patient, (e.g., devices implanted more than two to three centimeters below the skin or outer surface of the patient).

The ability to quickly recharge the power source of an implanted medical device, for example within a one hour recharging period of time on a monthly or yearly cycle, without the need to explant the device to do so, allows at least the benefits described above, including use of a smaller power source to help miniaturize the implantable medical device itself, and to allow more power, and thus greater functionality for the implanted medical device by providing an overall longer mission lifespan for the device using a smaller sized power source. Examples of the multi-axis antenna as described in this disclosure have been shown to provide recharging currents in devices implanted at about fifteen centimeters within a body of a patient, and to charge a 20 milliamp-hour (mAh) battery of the implanted device in about sixty minutes. Such examples include three coils wound on a ferrite core, the core having a cubic shape and dimensions of three-millimeters by three-millimeters by three-millimeters, the magnetic fields having a random orientation relative to the orientation of the implanted device.

Throughout the disclosure reference is made to a "magnetic field" or to "magnetic fields" in the context of a magnetic field or magnetic fields that is/are generated externally to an implantable medical device, and imposed onto the implanted medical device for the purpose of inducing a current into one or more coil windings of a receive antenna configuration of the implantable medical device. Examples of waveforms that may represent one or more parameters of a magnetic field or magnetic fields are illustrated and described with respect to FIG. 9. However, the examples of magnetic field(s) are not limited to magnetic fields(s) having the particular waveforms illustrated in FIG. 9. Any magnetic field or magnetic fields having a parameter (e.g., amplitude or phase) of the magnetic field that varies in time, or that varies in time with respect to the magnetic field direction of the magnetic field, such that a time rate of change of the net magnetic flux intensity imposed onto the coil windings of the receive antenna configuration, and a corresponding change in the electro-motive force (emf) configured to generate a current or currents in the one or more coil windings is contemplated by the use of the terms "magnetic field" and "magnetic fields" throughout this disclosure.

FIG. 1 is a conceptual drawing illustrating an example medical device system 10 in conjunction with a patient 12 according to various examples described in this disclosure.

The systems, devices, and methods described in this disclosure may include examples of a multi-axis antenna located within or electrically coupled to an implanted medical device, and provide for charging of these internal, and in some instances deeply implanted device, such as IMD 15A, IMD 15B, and/or sensor circuits 18, as illustrated and described with respect to FIG. 1. For purposes of this description, knowledge of cardiovascular anatomy is presumed, and details are omitted except to the extent necessary or desirable to explain the context of the techniques of this disclosure. The systems, devices, and methods described herein may provide efficient coupling for recharging power sources internal to IMD 15A, IMD 15B, and/or sensor circuits 18, even when these devices are deeply implanted within the patient. The implanted devices may include multi-axis antennas that are not necessarily orientation specific with respect to coupling efficiencies between the antenna of the device being inductively recharged and the orientation of one or more coils being used to provide the magnetic field or fields being imposed on the device for the purpose of inductively recharging a power source, such as a battery, located within the device. In various examples, IMD 15A and/or IMD 15B may represent examples of a defibrillator, a cardiac resynchronization pacer/defibrillator, or a pacemaker. The medical device system 10 typically includes provisions for interrogating these devices through a wireless or other communication protocol using an external "instrument" that includes an external-to-the-patient antenna and software/firmware interface to collect data.

In some existing examples of implantable medical devices, techniques used to keep the size dimensions of the device as small as possible include use of a planar antenna (receiving/transmitting antenna), for example an antenna comprising a conductive trace printed on a planar surface such as a substrate, provided within the implantable medical device. One possible advantage of a planar antenna design, as compared to for example a multi-axis antenna, is that the uni-directional or planar format of the antenna may take up less space within the device, and may be more easily packaged into the device when size and space are of concern. A disadvantage associated with the planar antenna may be that coupling efficiencies with respect to receiving power transmitted from outside patient to the antenna may be orientation specific. For example, the orientation of the electromagnetic and magnetic fields being imposed on an implanted medical device relative to the orientation (e.g., a normal axis of orientation) of a planar-type receive antenna within the implanted medical device may have an effect on the efficiency of transferring power from the electromagnetic and magnetic fields to the receive antenna.

For some implanted devices, the orientation of the implanted device, and thus the orientation of the receive antenna may not be precisely known, or may shift at some point in time after implantation of the device into a patient. This shifting of position may include movement of the device itself during the time when recharging of the device is being performed. Such shift in position may be caused by motions of tissue in the area of the implantation, such as cardiac activity including heartbeats of the heart of the patient, and/or movements of the patient themselves, such as when the patient is walking, standing, or changing position, such as movements while lying down. Such changes in orientation of the implanted medical device may cause issues, including variations in the power transfer efficiencies, while attempting to inductively recharge a power source, such as a battery, that is located within the implanted medical device.

Examples of compact multi-axis antennas as described herein may overcome some or all of these orientation issues related to coupling efficiencies and recharging of an implanted medical device. For example, use of the multi-axis antennas as described in this disclosure within or coupled to an implantable medical device may minimize or even eliminate the issues related to the orientation of the antenna relative to one or more recharging coils being used to provide the magnetic fields inducing current in the antenna. Because the examples of multi-axis antennas as described in this disclosure are not generally orientation specific, for example as a planar antenna might be, a recharging process performed on the implanted medical device having the multi-axis antenna may be performed by a single planar recharging coil, a simple wound non-planer coil, a helical planer or non-planer, or single pair of recharging coils, arranged for example as a Helmholtz coil. A higher level of coupling efficiency may be achievable between the recharging coil(s) and the multi-axis antenna during the recharging process regardless of the relative orientation of the recharging coils relative to the multiple-axis antenna, for example compared to an implanted medical device having a uni-directional antenna and a same relative orientation between the uni-directional antenna and the recharging coil(s).

In the illustrated example of FIG. 1, medical device system 10 includes an implantable medical device (IMD) 15A coupled to a ventricular lead 22 and an atrial lead 21. IMD 15A may include an example of a multi-axis antenna as described herein, the multi-axis antenna configured to have currents induced into the multi-axis antenna by one or more magnetic fields provided externally to the patient 12, the induced current for use in recharging a power source within IMD 15A. In various examples, IMD 15A is an implantable cardioverter-defibrillator (ICD) capable of delivering pacing, cardioversion and defibrillation therapy to the heart 13 of a patient 12. Ventricular lead 22 and atrial lead 21 are electrically coupled to IMD 15A, and extend into the heart 13 of patient 12. Ventricular lead 22 includes electrodes (not labeled in FIG. 1) positioned on the lead in the patient's right ventricle (RV) for sensing ventricular EGM signals and pacing in the RV. Atrial lead 21 includes electrodes (not labeled in FIG. 1) positioned on the lead in the right atrium (RA) of patient 12 for sensing atrial EGM signals and pacing in the RA. Ventricular lead 22 and/or atrial lead 21 may also include coil electrodes used to deliver cardioversion and defibrillation shocks. The term "anti-tachyarrhythmia shock" may be used herein to refer to both cardioversion shocks and defibrillation shocks. IMD 15A may use both ventricular lead 22 and atrial lead 21 to acquire cardiac electrogram (EGM) signals from patient 12 and to deliver therapy in response to the acquired data. Medical device system 10 is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, a multi-axis antenna, a rechargeable power source, and other circuitry configured for performing the techniques described herein or otherwise ascribed to IMD 15A may be housed within a sealed housing 23. Housing 23 (or a portion thereof) may be conductive so as to serve as an electrode for pacing or sensing, or as an active electrode during defibrillation. As such, housing 23 is also referred to herein as "housing electrode" 23. Housing 23 may include one or more electrodes with a high-capacitance portion and a low-capacitance portion. The high-capacitance portion and the low-capacitance portion may be formed using two different materials.

IMD 15A may transmit EGM signal data and cardiac rhythm episode data, as well as data regarding delivery of therapy by IMD 15A, to an external device 11. External device 11 may also be referred to as an "instrument," which may include any of the devices described throughout the disclosure as devices located externally to the patient, and in some examples may be included as part of a recharging system configured to recharge the battery or other power source provided within IMD 15A. For example, external device 11 as illustrated in FIG. 1 may be a computing device, e.g., used in a home, ambulatory, clinic, or hospital setting, to communicate with IMD 15A via wireless telemetry. External device 11 may be coupled to a remote patient monitoring system, such as Carelink®, available from Medtronic plc, of Dublin, Ireland. External device 11 may be, as examples, a programmer, external monitor, or consumer device, e.g., a smart phone.

External device 11 may be used to program commands or operating parameters into IMD 15A for controlling its functioning, e.g., when configured as a programmer for IMD 15A. External device 11 may be used to interrogate IMD 15A to retrieve data, including device operational data as well as physiological data accumulated in IMD 15A memory. The interrogation may be automatic, e.g., per a schedule, or in response to a remote or local user command. Examples of communication techniques used by IMD 15A and external device 11 may include tissue conductance communication (TCC) and/or radio frequency (RF) telemetry, which may be an RF link established via Bluetooth®, WiFi, or medical implant communication service (MICS).

As illustrated in FIG. 1 the medical device system 10 may also include an intracardiac pacing device IMD 15B. IMD 15B may include an example of a multi-axis antenna as described herein, the multi-axis antenna configured to have currents induced into the multi-axis antenna by one or more magnetic fields provided externally to the patient 12, the induced currents for use in recharging a power source within IMD 15B. In the illustrated example, IMD 15B is implanted in the right ventricle of patient 12, e.g., internal to the heart 13 of patient 12. In some examples, one or more IMDs like IMD 15B (not shown in FIG. 1) may additionally or alternatively be implanted within other chambers of heart 13, or attached to the heart epicardially. IMD 15B may be configured to sense electrical activity of heart 13 and deliver pacing therapy, e.g., bradycardia pacing therapy, cardiac resynchronization therapy (CRT), anti-tachycardia pacing (ATP) therapy, and/or post-shock pacing to heart 13. IMD 15B may be attached to an interior wall of heart 13 via one or more fixation elements (not shown in FIG. 1), that penetrate the cardiac tissue. These fixation elements may secure IMD 15B to the cardiac tissue and retain an electrode (e.g., a cathode or an anode) on the housing of IMD 15B in contact with the cardiac tissue. In addition to delivering pacing pulses, IMD 15B may be capable of sensing electrical signals using the electrodes carried on the housing of IMD 15B. These electrical signals may be electrical signals generated by cardiac muscle and indicative of depolarizations and repolarizations of heart 13 at various times during the cardiac cycles of heart 13.

In some examples, IMD 15A and IMD 15B may both be configured to deliver pacing therapy. In such examples, IMD 15A and IMD 15B may delivery pacing therapy to the right and/or left ventricles of heart 13, respectively, to provide CRT pacing. Additionally, IMD 15A and IMD 15B may both be configured to detect tachyarrhythmias, and deliver anti-tachyarrhythmia therapy. IMD 15A and IMD 15B may be configured to coordinate their cardiac rhythm detection and treatment activities. In some examples, IMD 15A and IMD 15B may engage in wireless communication between IMD 15A and IMD 15B to facilitate such coordinated activity. The wireless communication may by via TCC, and may be one-way communication in which one device is configured to transmit communication messages and the other device is configured to receive those messages, or two-way communication in which each device is configured to transmit and receive communication messages.

In various examples, IMD 15B is configured to wirelessly communicate directly with external device 11, using any of the communication protocols described above with respect to IMD 15A. External device 11 may be, as examples, a programmer, external monitor, or consumer device, e.g., a smart phone, that may be used to program commands or operating parameters into IMD 15B for controlling the functioning of the device. External device 11 may be used to interrogate IMD 15B to retrieve data, including device operational data as well as physiological or neurological data accumulated in memory of IMD 15B. The interrogation may be automatic, e.g., according to a schedule, or in response to a remote or local user command. In some examples, communication between IMD 15B and external device 11 may take place through IMD 15A, wherein IMD 15B communications with IMD 15A, and IMD 15A communicates with external device 11. Examples of communication techniques used by IMD 15A and/or 15B and external device 11 are not limited to any particular communication technique or communication protocol, and in some examples TCC or RF telemetry, which may be an RF link established via Bluetooth®, WiFi, or medical implant communication service (MICS).

In various examples, communications provided from IMD 15A and/or IMD 15B may include data and/or other information related to the inductive charging of these devices. For example, when an electromagnetic or magnetic field is imposed on IMD 15A and/or IMD 15B for the purpose of inductively charging these device(s), information related to the coupling efficiency of inductive coupling to the device, and/or for example the state of charge (e.g., percent of charge relative to a full charge) may be transmitted from one or both of IMD 15A and/or IMD 15B to external device 11 as part of the recharging process. Other information, such as time to full charge, rate of recharge, and temperature of the device may also be provided as transmitted information from the device(s) being recharged. In some examples, this information may be used to adjust parameters, such as the field strength of the fields used to induce the energy in the antenna for recharging of IMD 15A and/or IMD 15B, or for example to provide information used to reconfigure the electrical parameters being used to energize the coil or coils that are providing the fields used for the inductively coupled recharging of these device(s).

In addition, information may be provided by IMD 15A and/or IMD 15B that is indicative of the level of the recharging of one or both of IMD 15A and/or IMD 15B that has been achieved or completed, which may then be used to determine when to further regulate, stop, or otherwise terminate the recharging process. For example, during the recharging process IMD 15A and/or IMD 15B may transmit data or other information indicating that the device, respectively, is fully recharged. The indication may then be used by the external devices providing the fields (not show in FIG. 1) to stop the charging process, which may include removing the fields used to recharge IMD 15A and/or IMD 15B from being imposed on these devices. In addition, monitoring the temperature of these devices may be important, as overheating of an implanted device as a result of the recharging process may damage the device, or present a safety issue for the patient. Adjustments to the intensities of the fields being imposed on the device(s), and/or termination of the recharging process altogether may be made based on the monitored temperature of the device being recharged as a part of the recharging process.

In various examples, one or more additional sensor circuits may be located outside of or separately located relative to the IMD 15A and/or IMD 15B. These one or more additional sensor circuits are illustratively represented by sensor circuits 18. Sensor circuits 18 may include a single sensor circuit configured to sense a particular physiological or neurological parameter associated with patient 12, or may comprise a plurality of sensor circuits, which may be located at various and/or different positions relative to patient 12 and/or relative to each other, and may be configured to sense one or more physiological parameters associated with patient 12.

For example, sensor circuits 18 may include a sensor operable to sense a body temperature of patient 12 in a location of the sensor circuits 18, or at the location of the patient where a temperature sensor coupled by a lead to sensor circuits 18 is located. In another example, sensor circuits 18 may include a sensor configured to sense motion, such as steps taken by patient 12 and/or a position or a change of posture of patient 12. In various examples, sensor circuits 18 may include a sensor that is configured to detect breaths taken by patient 12. In various examples, sensor circuits 18 may include a sensor configured to detect heartbeats of patient 12. In various examples, sensor circuits 18 may include a sensor that is configured to measure systemic blood pressure of patient 12.

In some examples, one or more of the sensors comprising sensor circuits 18 may be implanted within patient 12, that is, implanted below at least the skin level of the patient. In some examples, one or more of the sensors of sensor circuits 18 may be located externally to patient 12, for example as part of a cuff or as a wearable device, such as a device imbedded in clothing that is worn by patient 12. In various examples, sensor circuits 18 may be configured to sense one or more physiological parameters associated with patient 12, and to transmit data corresponding to the sensed physiological parameter or parameters to IMD 15A, as represented by the lightning bolt coupling sensor circuits 18 to IMD 15A. Transmission of data from sensor circuits 18 to IMD 15A in various examples may be performed via wireless transmission, using for example any of the formats for wireless communication described above. In various examples, transmission of data from one or more of the sensors comprising sensor circuits 18 to IMD 15A may be performed by a wired connection between the sensor circuits 18 and IMD 15A. When sensor circuits 18 are implanted devices that are implanted within patient 12, one or more of the sensor circuits may include any examples of the multi-axis antenna described in this disclosure, and the recharging techniques as described throughout this disclosure may be used to also recharge a power source, such as a battery, located within the implanted sensor(s) that is configured to provide power to operate the sensor.

In various examples, IMD 15A and or IMD 15B may communicate wirelessly to an external device (e.g., an instrument or instruments) other than or in addition to external device 11, such as transceiver 16 shown in FIG. 1. In various examples, transceiver 16 as shown in FIG. 1 is an access point, such as access point 145 illustrated and described with respect to FIG. 7, that provides a wireless communication link between IMD 15A and/or IMD 15B, and a network such as network 147 illustrated and described with respect to FIG. 7. In various examples, transceiver 16 is communication circuitry 224 of recharging system 200 shown in FIG. 8, wherein communication circuitry 224 is configured to communicate with IMD 15A and/or IMD 15B during the recharging process of these devices, as further described below. Examples of communication techniques used by any of the devices described above with respect to FIG. 1 and transceiver 16 may include radiofrequency (RF) telemetry, which may be an RF link established via Bluetooth®, WiFi, or medical implant communication service (MICS).

For the remainder of the disclosure, a general reference to a medical device system may refer collectively to include any examples of medical device system 10, a general reference to IMD 15 may refer collectively to include any examples of IMD 15A and/or IMD 15B, a general reference to sensor circuits may refer collectively to include any examples of sensor circuits 18, a general reference to external device may refer collectively to include any examples of external devices 11, and a general reference to a transceiver may refer collectively to any examples of transceiver 16.

Figure 2:
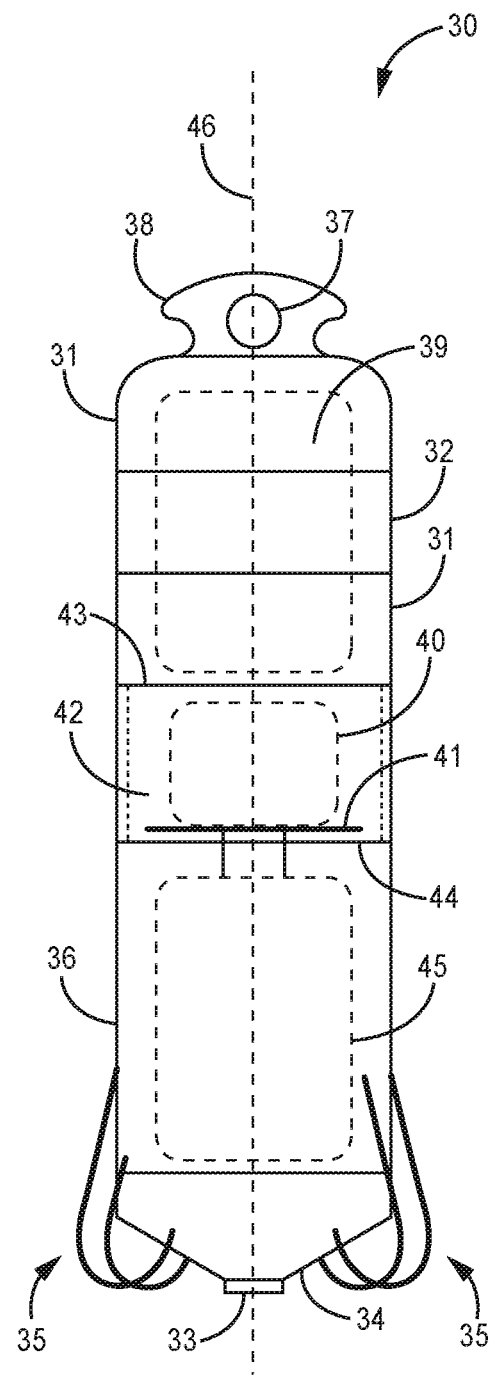
FIG. 2 is a conceptual drawing illustrating an example configuration of an implantable medical device according to various examples described in this disclosure.

FIG. 2 is a conceptual drawing illustrating an example configuration of an implantable medical device 30 according to various examples described in this disclosure. Device 30 in some examples is an intracardiac pacing device designed to be implanted within a chamber of the heart of a patient. Device 30 in some examples is IMD 15B as illustrated and described with respect to FIG. 1. Device 30 may be configured to be implanted in the right ventricle of the heart of a patient, as depicted in FIG. 1, or in some other chamber of the heart of a patient. As shown and described with respect to FIG. 2, device 30 may be an example of an implantable medical device that includes a multi-axis antenna 40 that may be used to provide a recharging current that is induced into the coils of the multi-axis antenna for the purpose of recharging a power source, such as battery 39, within device 30. In some examples, device 30 is a Medtronic® Micra™ Transcatheter Pacing System developed by Medtronic, plc, of Dublin, Ireland.

As shown in FIG. 2, device 30 includes first housing portion 31, an antenna window 42, a second housing portion 36, and an end cap 34 coupled together to form the external portions of device 30. First housing portion 31, antenna window 42, second housing portion 36, and end cap 34 may be "sealingly joined" together as shown in FIG. 2 to form a hermetically sealed housing that encloses a battery 39, a multi-axis antenna 40, and electronic circuitry 45 of device 30. As used herein, "sealingly coupled" or "sealingly joined" refers to two or more individual pieces of material that are mechanically coupled to one another at a joint or along a seam that is formed to provide a hermetic seal at the joint or seam between the two or more pieces. Device 30 as shown in FIG. 2 may further includes electrode 32, electrode 33, fixation mechanisms 35, and flange 38 including an opening 37. Both first housing portion 31, second housing portion 36, and end cap 34 may be formed from electrically insulating material, and/or may be coated with a polymer material such as a poly-para-xylylene (commonly "Parylene"). In some examples, one or both of first housing portion 31 and second housing portion 36 may be formed of same material including titanium. In some examples, end cap 34 may be formed in whole or in part from an electrically insulative material, such as a plastic material.

Although device 30 is generally described as including one or more electrodes, device 30 may typically include at least two electrodes (e.g., electrodes 32 and 33) to deliver an electrical signal (e.g., therapy such as cardiac pacing) and/or provide at least one sensing vector. Electrode 32 is carried on the portion device 30 indicated as first housing portion 31, and electrode 33 is carried at the upper or distal portion of end cap 34. Electrodes 32 and 33 may be considered leadless electrodes in the sense that they are not coupled to device 30 or a housing portion of device 30 by a lead. In the example of FIG. 2, electrode 32 may be a ring or cylindrical electrode disposed on the exterior surface of first housing portion 31, and electrode 33 may be disposed on the exterior surface of end cap 34. Electrode 33 may be a circular electrode positioned to contact cardiac tissue upon implantation of device 30. Electrode 33 may be used as a cathode and electrode 32 may be used as an anode, or vice versa, for delivering cardiac pacing such as bradycardia pacing, cardiac resynchronization therapy (CRT), antiachycardia pacing (ATP), or post-shock pacing. However, electrodes 32 and 33 may be used in any stimulation configuration. In addition, electrodes 32 and 33 may be used to detect intrinsic electrical signals from cardiac muscle tissue. Electrode 33 may be configured to contact cardiac tissue such as an interior wall of the right ventricle, when device 30 is implanted with the heart of a patient.

Fixation mechanisms 35 may be arranged to attach device 30 to cardiac tissue. Fixation mechanisms 35 may be active fixation tines, screws, clamps, adhesive members, or any other mechanisms for attaching a device to tissue. As shown in the example of FIG. 2, fixation mechanisms 35 may be constructed of a memory material, such as a shape memory alloy (e.g., nickel titanium), that retains a preformed shape. During implantation, fixation mechanisms 35 may be flexed forward to pierce tissue, and then allowed to flex back towards second housing portion 36. In this manner, fixation mechanisms 35 may be embedded within the target tissue to secure device 30 in place relative to the target tissue. A flange 38 may be provided on one end of device 30, for example extending from first housing portion 31, to enable tethering and/or extraction of device 30. For example, a suture or other device may be inserted around flange 38 and/or through opening 37 and attached to tissue. In this manner, flange 38 may provide a secondary attachment structure to tether or retain device 30, for example within the heart. Flange 38 and/or opening 37 may also be used to extract device 30 once the device needs to be explanted (or removed) from the patient if such action is deemed necessary.

Electronic circuitry 45, including communication and/or recharging circuitry coupled to the multi-axis antenna 40, and a power source such as battery 39, may be housed within the housing of device 30. The power source is not limited to any particular type of power source, and in some examples, is a rechargeable battery, which is coupled to the electronic circuitry 45 and is configured to provide electrical power to the electronic circuitry. The electronic circuitry 45 of device 30 is not limited to any particular type or arrangement of electronic devices, and may include any type(s) of devices arranged to perform any of the functions ascribed to device 30. For example, electronic circuitry 45 may include electronic devices configured to perform any of the patient monitoring functions and/or to provide electrical stimulation therapy through the electrodes (e.g., electrodes 32 and 33) of device 30. Electronic circuitry 45 may further include communication circuitry configured to provide wireless communication between device 30 and other devices, such as external device 11 and/or transceiver 16 as illustrated and described above for example with respect to FIG. 1. The communication circuitry of device 30 may utilize the multi-axis antenna 40 for transmission of signals transmitted from device 30, and for reception of signals transmitted to device 30 from one or more devices external to device 30.

In addition, multi-axis antenna 40 may be configured to receive electrical energy imposed on device 30 in the form of one or more magnetic fields, and to recharge battery 39 using energy inductively coupled to antenna 40 from these field(s), which may also be referred to as wireless power transfer. In order to achieve a high level of coupling efficiency between the antenna 40 and the magnetic field(s) being imposed on device 30 for the purpose of recharging battery 39, antenna 40 is arranged as a multi-axis antenna, for example including a first coil, a second coil and a third coil (not specifically shown in FIG. 2, but for example first coil 71, second coil 76, and third coil 80 as illustrated and described with respect to FIG. 4). As shown in FIG. 2, the multi-axis antenna 40 is positioned within device 30, for example relative to longitudinal axis 46 of device 30, to align with and in some examples be encircled by antenna window 42.

As further described below, the antenna window 42 may be formed of a material, for example a material having a high value relative to electrical resistivity, that allows for transmission of the electromagnetic energy being imposed onto device 30 for recharging purposes to penetrate and pass through the antenna window 42, and reach the antenna 40. The antenna window 42 may be referred to as being formed from a "radio transmissive" material that also provides a low relative dielectric constant (i.e., high relative electrical resistivity), and low magnetic permeability. Electrical resistivity may be represented by the Greek letter $\rho$ (rho), and in International System (SI) units is measured in ohm-meter ($\Omega \cdot m$), and which may vary for a given material based on temperature. An example of a material, such as certain metals, that may be considered to be a good electrical conductor and thus have a low value for electrical resistivity, is copper, having a $\rho$ value of approximately $1.68 \times 10^{-8}$ $\Omega \cdot m$ at 20 degrees Celsius (° C.). An example of a material that may be considered to be poor conductors of electricity, e.g., and electrical insulator, and thus having a high value for $\rho$ may include glass, which can have a $\rho$ value in a range of $10 \times 10^{10}$ to $10 \times 10^{14}$ $\Omega \cdot m$ at 20° C. Another example of a material having a high value for $\rho$ is sapphire, which in some examples has a $\rho$ value of $10^{14}$ $\Omega$/centimeter at 23° C.

In order to allow higher frequency magnetic fields to penetrate the housing of device 30 and reach antenna 40, at least the antenna window 42 portion of the device may be formed of a material, such as sapphire, that has a high value for electrical resistivity, at least at temperatures normally experienced by devices after being implanted within a patient, (e.g., temperatures normally not to exceed 39 to 40° C. on the exterior surface of the implanted device even for a brief period of time, such as when the device is being recharged. To allow use of higher frequency magnetic fields for the purpose of recharging device 30, antenna window 42 may be made of a radio transparent material having high electrical resistivity (e.g., in a range of $1\times10^{11}$ to $1\times10^{16}$ Ohms/centimeter) and a low magnetic permeability. A wide range of materials will satisfy these requirements, examples such as sapphire, a glass material, or polymeric materials are typically employed having a dielectric constant ranging from about 1 to 12, Use of sapphire or a glass material for antenna window 42 may allow a higher frequency of an induced magnetic field to be transmitted through the antenna window 42 and be imposed on antenna 40 relative to other materials that may not provide a same level, or as high a value, for electrical resistivity. For example, by using an antenna window 42 made from sapphire, magnetic fields having frequencies ranging from about 100 KHz to 10 MHz be imposed on device 30, wherein the sapphire allows the imposed magnetic field or fields to pass through the antenna window 42 and induce a current in one or more of the coils forming multi-axis antenna 40. The ability to use higher frequency magnetic fields allows for more energy, and thus a larger current, to be induced into the coil or coils of antenna 40 at any given time, or over a particular time period during which the higher frequencies are being imposed on device 30, as compared to using a lower frequency magnetic field. Antenna window 42 is not limited to being formed from a visually transparent material. Examples of material used to form antenna window 42 may include any type of material having a minimum value for electrical resistivity (e.g., a good electrical insulator with low dielectric constant value) and low magnetic permeability, and that meets other manufacturing requirements and complies with any other applicable regulatory requirements, such as biocompatibility requirements, for use in implantable medical devices.

As illustrated in FIG. 2, first housing portion 31 is sealingly coupled to antenna window 42 at a first seam 43. The antenna window 42 is sealingly coupled to the second housing portion 36 of device 30 at second seam 44. Antenna 40 may be positioned within the portion of device 30 that is encircled by the antenna window 42. The electronic circuitry 45 may be positioned within the portion of device 30 encircled by second housing portion 36. End cap 34 may be sealingly coupled to the end of second housing portion 36 that is opposite the end of second housing portion 36 coupled to the antenna window 42.

Examples of antenna window 42 are not limited to being formed from a material that is different from the first housing portion 31 and/or different from the second housing portion 36. In some examples, the antenna window 42 and the second housing portion 36 may be formed of a same material, such as sapphire, that is a different material used to form the first housing portion 31. In some examples, the first housing portion 31, the antenna window 42, and the second housing portion 36 are all formed of a same material, such as titanium or a titanium alloy, and may be formed as a single piece, or as separate pieces sealingly joined together.

Because antenna 40 is arranged as a multi-axis antenna, the direction, e.g., the orientation of the imposed magnetic field or magnetic fields reaching antenna 40 may provide a minimum level of coupling efficiently between the antenna and the field(s) regardless of the relative orientation of device 30 and the direction of orientation of the imposed magnetic field(s). In order words, the antenna 40 itself may not be orientation specific with respect to the orientation of antenna 40 relative to the orientation of the fields imposed on device 30 for the purpose of inductive power transfer that can be used for recharging of battery 39. For example, any angle of direction for a magnetic field imposed on device 30 may induce some level of current within antenna 40 for a given level of the magnetic field strength imposed on device 30 and thus on antenna 40. The specific angle of the direction of the actual magnetic field in some examples of devices may be irrelevant with respect to the level of current induced in antenna 40 for a given level of energy of the magnetic field or fields.

In some examples, various other aspects of the device 30 itself, such as interference with the transmission of the magnetic field created by first housing portion 31, and/or second housing portion 36, or for example by materials used to form certain portion of device 30 (e.g., a titanium material used to form a cover for battery 39), may result in a lower level of induced currents when the magnetic fields are imposed at certain angles relative to the device compared to other angles for imposing the magnetic field onto the device. For devices where certain angles of the direction of the actual magnetic field being imposed on the device may incur interference with the inductive coupling of the magnetic field with the multi-axis antenna of the device, some level of current or currents may still be induced into the multi-axis antenna, but may for example provide a lower level of induced current compared to other angles of direction of the actual magnetic field that may be used to impose the magnetic field onto the multi-axis antenna. In such instances, a feedback signal provided by the device having the multi-axis antenna and that is indicative of the level of induced current(s) being generated by the multi-axis antenna may be used to reorient the direction of the magnetic fields relative to the device. Based on monitoring the feedback signal, a different relative angle between the device and the direction of the magnetic fields can be arranged, for example by moving the position of the transmit coil(s) providing the magnetic field, and thus may provide a better level of inductive coupling between the magnetic field and the multi-axis antenna.

Based on the capability of multi-axis antenna 40 to provide at least a minimum level of induced current from the antenna for a given power level of a magnetic field being imposed onto the antenna regardless of the angle of incidence (orientation) of the magnetic field relative to the antenna within the bounds determined by other physical factors related to the device itself, a specific orientation between antenna 40 and the direction of the incident magnetic field imposed on antenna 40 is not required. The minimum current level may be induced into one or more of the coils of multi-axis antenna 40 regardless of the specific orientation of the incident magnetic field and the relative orientation of the multi-axis antenna to those magnetic field(s). This feature is useful when performing a recharging operation on an implanted device that includes a multi-axis antenna within the device because a minimum level of recharging current can be induced into the antenna of the device without the need for an elaborate or complex alignment procedure to orient the magnetic fields to a particular orientation of the device and the antenna. For deeply implanted devices whose exact orientation may not be known, or whose position may have shifted, or may actually be shifting during a recharging session of the device, the feature of not having to determine this relative orientation may allow less expensive, less complicated, and less time-consuming techniques to be used to efficiently recharging the power source located within the implanted device.

While examples of induced current as described above have been described with respect to recharging a power source located within the device, the multi-axis antenna and features of inductive power transfer to the device through current induced in the multi-axis antenna may also be applied when inducing a current into the antenna for the purpose of providing electrical energy to directly power the operation of the device itself, for example in a passive device that may only operate when powered by external power source.

As shown in FIG. 2, power source (battery) 39 is comprises some portion of the device such as first housing portion 31, antenna 40 is located within an interior space encircled by antenna window 42, and electronic circuitry 45 is located substantially within the interior space of device 30 formed by second housing portion 36. Examples of the arrangement of the devices within the housing of device 30 are not limited to the arrangement as shown in FIG. 2, and other arrangements of the devices and components included within device 30 are contemplated for use with the multi-axis antenna described in this disclosure. For example, as shown in FIG. 2 antenna 40 is arranged on a substrate or other planar surface, which in some examples is a circuit board 41. Electrical conductors may extend from circuit board 41 and be electrically coupled to the electronic circuitry 45, and/or to one or more terminals of battery 39. In other examples, antenna 40 is physically coupled to a separate circuit board such as circuit board 41. In some examples, portions of circuit board 41 may be formed as part of a larger circuit board, or as a substrate that may also include other electrical devices, such as electrical devices utilized as part of the recharging circuitry of device 30 and/or electrical devices of electronic circuitry 45.

In some examples of device 30, first housing portion 31, antenna window 42, and second housing portion 36 may not be separately formed pieces, but instead may be one piece formed from a same type of material, and sealingly coupled to end cap 34 to form the hermetically sealed housing for device 30. In such examples, antenna window 42 is not provided as a separate piece of material, and instead is considered to be formed of the same material forming the one piece of material forming the housing portions of device 30. Device 30 is not limited to a device having any particular shaped housing. As shown in FIG. 2, device 30 has a generally circular cross-sectional shape along longitudinal axis 46 for any plane that is perpendicular to longitudinal axis 46 throughout the first housing portion 31, antenna window 42, and second housing portion 36. In some examples, the circular cross-sectional shape of device has a diameter of approximately six millimeters. However, device 30 is not limited to having a circular cross-sectional shape as described above, and portions of device 30 may have other shapes in cross-section relative to longitudinal axis 46, including a rounded square, a rounded rectangle, or an elliptical shape. Additional examples of multi-axis antenna that may be provided as antenna 40 in device 30 and systems and techniques to recharge device 30 are illustrated and described below with respect to FIGS. 3-11.

Figure 3:
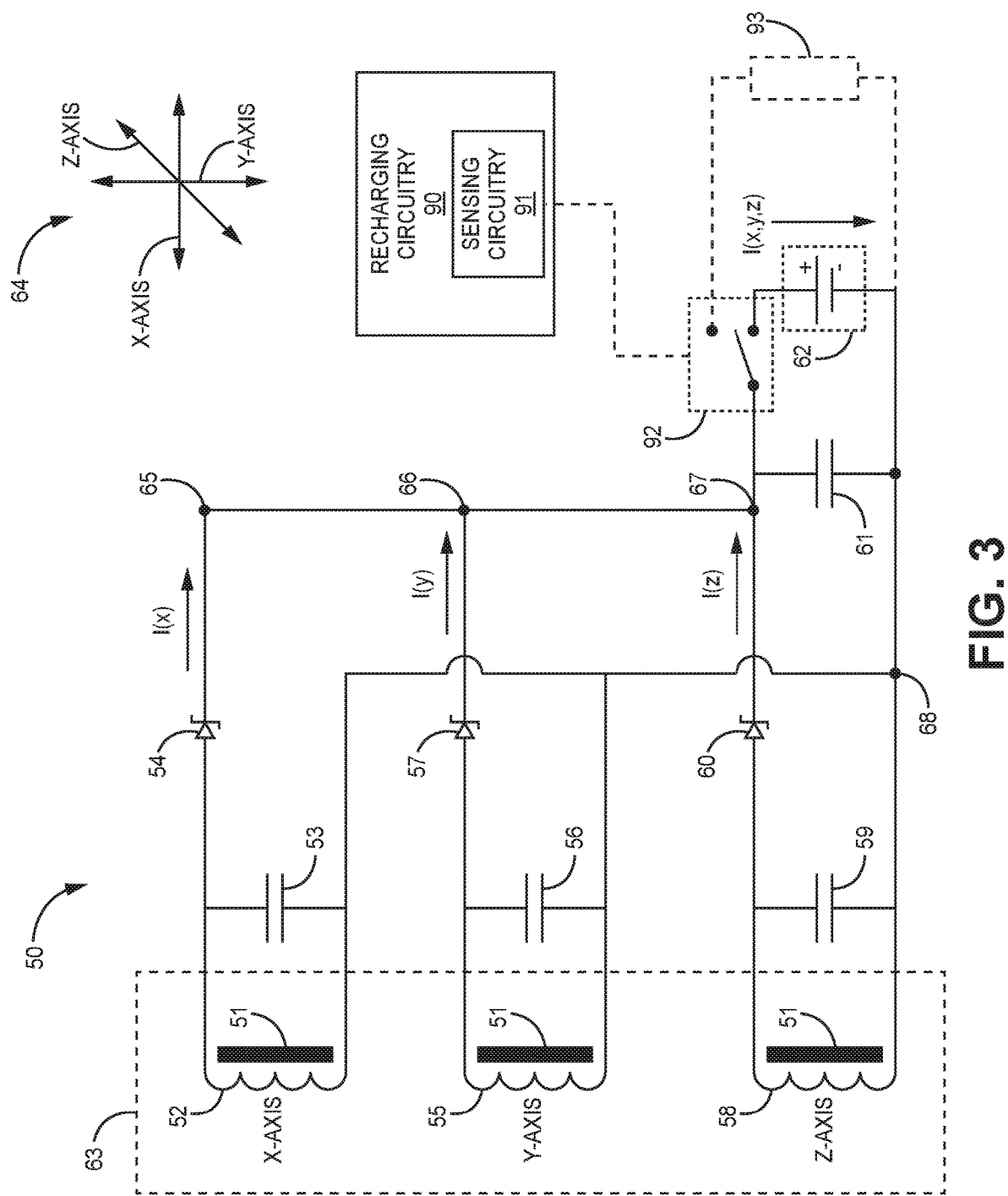
FIG. 3 is a schematic diagram including a three-axis antenna coupled to a rechargeable power source of an implantable medical device according to various examples described in this disclosure.

FIG. 3 illustrates a schematic diagram 50 including a three-axis antenna 63 coupled to a rechargeable power source 62 of an implantable medical device according to various examples described in this disclosure. The three-axis antenna 63 and/or the additional circuitry illustrated in FIG. 3 may be representative of a multi-axis antenna that is included within or may be coupled to an implantable medical device such as IMD 15A or IMD 15B as shown in FIG. 1, or device 30 as shown in FIG. 2. As shown in FIG. 3, antenna 63 includes a first coil 52, a second coil 55, and a third coil 58, each coil formed in conjunction with a ferrite core 51 common to all three coils.

First coil 52 may be formed as a winding encircling a portion of ferrite core 51. First coil 52 may be wound from an electrical conductor, such as a conductive wire, that is wound around ferrite core 51 so that a magnetic field imposed on the antenna 63 having a magnetic field direction that is colinear with the X-axis of the three-axis coordinate system 64 provides a maximum level of coupling efficiency between the magnetic field and the first coil 52. First coil 52 may therefore also be referred to as the X-axis coil, and considered to have an axis of orientation, (e.g., a normal axis) that aligns with the X-axis of three-axis coordinate system 64.

Second coil 55 of antenna 63 may be wound from a separate electrical conductor relative to the electrical conductor used to form the first coil 52. The electrical conductor used to form the second coil 55 may be a same type of electrical conductor, such as a same type of conductive wire, as used to form the first coil 52. The electrical conductor of second coil 55 may be wound around ferrite core 51 so that that a magnetic field imposed on the antenna 63 having a magnetic field direction that is colinear with the Y-axis of the three-axis coordinate system 64 provides a maximum level of coupling efficiency between the magnetic field and the second coil 55. Second coil 55 may therefore also be referred to as the Y-axis coil, and considered to have an axis of orientation, (e.g., a normal axis) that aligns with the Y-axis of three-axis coordinate system 64.

Third coil 58 of antenna 63 may be wound from a separate electrical conductor relative to the electrical conductors used to form the first coil 52 and the second coil 55. The electrical conductor used to form the third coil 58 may be a same type of electrical conductor, such as a same type of conductive wire, used to form the first coil 52 and the second coil 55. The electrical conductor of third coil 58 may be wound around ferrite core 51 so that that a magnetic field imposed on the antenna 63 having a magnetic field direction that is colinear with the Z-axis of the three-axis coordinate system 64 provides a maximum level of coupling efficiency between the magnetic field and the third coil 58. Third coil 58 may therefore also be referred to as the Z-axis coil, and considered to have an axis of orientation, (e.g., a normal axis) that aligns with the Z-axis of three-axis coordinate system 64.

The relative physical arrangement and orientation of each of the first coil 52, the second coil 55, and the third coil 58 may be such that a magnetic field imposed on these coils at some angle that is not necessarily colinear with the corresponding X, Y, or Z-axis (and thus not necessarily providing maximum coupling efficiency for any given one of the coil), may still generate an induced current in one, two, or all three of these coils. The sum of these induced currents may be at least equal to a minimum level of current that would be induced in any one of these coils in instances where the direction of the magnetic field imposed on the coils is colinear with one of the X, Y, or Z-axis of coordinate system 64. As such, the particular orientation of antenna 63 may become irrelevant relative to the orientation of the magnetic field imposed on the antenna for the purpose of inducing at least a minimum level of current, for example a recharging current, into antenna 63 for a given magnetic field having a given field strength.

As shown in FIG. 3, a capacitor 53 is coupled in parallel with the first coil 52. Capacitor 53 may be sized with respect to a capacitance value so that in conjunction with first coil 52, a tank circuit is formed having a resonant frequency that matches a frequency that may be applied by externally generated magnetic field(s) imposed onto first coil 52 for the purpose of inducing a current into first coil 52. Having the tank circuit comprising first coil 52 and capacitor 53 tuned to have a resonate frequency that matches a frequency of the magnetic field(s) intended to be imposed onto the first coil 52 allows a higher level of coupling efficiency to be achieved between the imposed magnetic field(s) and the first coil 52 compared to other frequencies that are not matched to the resonate frequency of the tank circuit. A diode 54 is coupled in series with a first end of first coil 52 and a terminal of the capacitor 53. A second end of first coil 52 is coupled to a common voltage node 68. Diode 54 in some examples is a Schottky diode. Diode 54 is configured to rectify any current flows induced in first coil 52 so that all current flows generated in the first coil 52 as a result of externally imposed magnetic field(s) will flow through diode 54 in the direction indicated as "I(x)," and toward node 65. In some examples, a minimum level of voltage is required to forward bias diode 54, and therefore no current will be provided as current flow I(x) until the minimum voltage level required to forward bias diode 54 is present, resulting in a minimum initial level of current flow being provided by the current induced into first coil 52.

Similarly, a capacitor 56 may be coupled in parallel with the second coil 55. Capacitor 56 may be sized with respect to a capacitance value so that in conjunction with second coil 55, a tank circuit is formed having a resonant frequency that matches an intended frequency that may be applied by externally generated magnetic field(s) imposed onto second coil 55 for the purpose of inducing a current into second coil 55. The tank circuit comprising second coil 55 and capacitor 56 may be tuned to have a resonate frequency that matches the frequency of the magnetic field(s) intended to be imposed onto the second coil 55 to provide a higher level of inductive coupling efficiency as described above with respect to first coil 52. A diode 57 is coupled in series with a first end of second coil 55 and a terminal of the capacitor 56. A second end of second coil 55 is coupled to the common voltage node 68. Diode 57 in some examples is a Schottky diode. Diode 57 is configured to rectify any current flows induced in second coil 55 so that all current flows generated in the second coil 55 as a result of externally imposed magnetic field(s) will flow through diode 57 in the direction indicated as "I(y)," and toward node 66. In some examples, a minimum level of voltage is required to forward bias diode 57, and therefore no current will be provided as current flow I(y) until the minimum voltage level required to forward bias diode 57 is present, resulting in a minimum initial level of current flow being provided by the current induced into second coil 55.

As illustrated in schematic diagram 50, a capacitor 59 is coupled in parallel with the third coil 58. Capacitor 59 may be sized with respect to a capacitance value so that in conjunction with third coil 58, a tank circuit is formed having a resonant frequency that matches an intended frequency that may be applied by externally generated magnetic field(s) imposed onto third coil 58 for the purpose of inducing a current into third coil 58. The tank circuit comprising third coil 58 and capacitor 59 may be tuned to have a resonate frequency that matches the frequency of the magnetic field(s) intended to be imposed onto the third coil 58 to provide a higher level of inductive coupling efficiency as described above with respect to first coil 52 and second coil 55. A diode 60 is coupled in series with a first end of third coil 58 and a terminal of the capacitor 59. A second end of third coil 58 is coupled to the common voltage node 68. Diode 60 in some examples is a Schottky diode. Diode 60 is configured to rectify any current flows induced in third coil 58 so that all current flows generated in the third coil 58 as a result of externally imposed magnetic field(s) will flow through diode 60 in the direction indicated as "I(z)," and toward node 67. In some examples, a minimum level of voltage is required to forward bias diode 60, and therefore no current will be provided as current flow I(z) until the minimum voltage level required to forward bias diode 60 is present, resulting in a minimum initial level of current flow being provided by the current induced into third coil 58.

In addition to rectifying current, diodes 54, 57, and 60 also prevent current flows from one of coils 52, 55, and 58 from being backward driven into another one of the coils. For example, diode 54, by having the cathode of the diode coupled to node 65, will block any I(y) current provided by second coil 55, and any I(z) current provided by third coil 58, from being driven through first coil 52. Diode 57, by having the cathode of the diode coupled to node 66, will block any I(x) current provided by first coil 52, and any I(z) current provided by third coil 58, from being driven through second coil 55. Diode 60, by having the cathode of the diode coupled to node 67, will block any I(x) current provided by first coil 52, and any I(y) current provided by second coil 55, from being driven through third coil 58. As a result, any currents provided by first coil 52 as current I(x), will be summed together with any currents provided by second coil 55 as current I(y) and any currents provided by third coil 58 as current I(z). The sum of currents I(x), I(y), and I(z) will be provided at node 67.

A smoothing capacitor 61 may be coupled between node 67 and the common voltage node 68 to smooth out any rapid variations in the current provided to node 67. In addition, a power source 62 is coupled to node 67 through switching device 92. Switching device 92 is not limited to any particular type of device, and in some examples, may be a semiconductor device, such as a transistor, that is controlled by recharging circuitry 90. When switching device is operated to couple node 67 to power source 62 as shown in FIG. 3, current flows provided as current flows I(x), I(y), and I(z) may be provided to a first terminal of power source 62 through switching device 92 from node 67. A second terminal of power source 62 is coupled to the common voltage node 68. When coupled to node 67, a flow of current from node 67 may be provided as current I(x,y,z) at the first terminal of power source 62, and provide a source of electrical energy to recharge power source 62. In various examples, recharging circuitry 90 is configured to control the coupling of node 67 to power source 62 by controlling switching device 92, and thus regulate and control the rate and intervals during which power source 62 receives the current flow from node 67.

Recharging circuitry 90 may include sensing circuitry 91. Sensing circuitry 91 may include sensors and sensor processing circuitry (not shown in FIG. 3) configured for example to sense one or more parameters associated with the operation of the devices illustrated in FIG. 3. For example, sensing circuitry 91 may include one or more sensors configured to sense a level of current flow being provided by one or more of coils 52, 55, and 58 as current I(z), I(y), and/or I(z). Sensing circuitry 91 may include one or more sensors configured to sense a level of current flow being provided to power source 62 as current I(x,y,z). Sensing circuitry 91 may also include one or more sensors configured to sense other parameters, such as the temperature of power source 62 and/or a temperature within the device where antenna 63 and power source 62 are located. Recharging circuitry 90 may be configured to receive electrical signals and/or data derived from the electrical signals that are sensed using sensing circuitry 91, and to control the recharging of power source 62 based at least in part of these sensed signal and/or the information derived from these sensed signals.

Sensing circuitry 91 may include on or more sensors configured to measure a voltage level and/or a level of recharge present at power source 62. Electrical signals and/or information derived from electrical signals sensed by sensing circuitry 91 that indicate of the voltage level and/or a level of recharging that has been competed relative to power source 62 may also be utilized by recharging circuitry 90 as a basis for controlling the recharging of power source 6. For example, recharging circuitry may utilize these signals and/or information derived from these signals as a basis by to regulate the current being provided to power source 62 from node 67 by controlling the coupling provided between node 67 and power source 62 through switching device 92.

In some examples, a shunt device 93, which may comprise an electrically resistive load, may be coupled to switching device 92 such that switching device 92 may couple the shunt device 93 to node 67. The coupling of shunt device 93 to node 67 may be utilized to dissipate the current, and thus the energy being imposed on coil 52, 55, and 58, at various times when recharging circuitry 90 determines that recharging current is not to be applied to power source 62 but wherein a recharging current is being induced into one or more of the coils. In some examples, recharging circuitry 90 may disconnect the coupling between node 67 and power source 62 when a determination is made that the recharging of power source 62 should be terminated, either on a temporary or a permanent basis. When not coupling node 67 to power source 62, recharging circuitry 90 and switching device 92 may be configured to optionally couple or not couple shunt device 93 to node 67.

Figure 4:
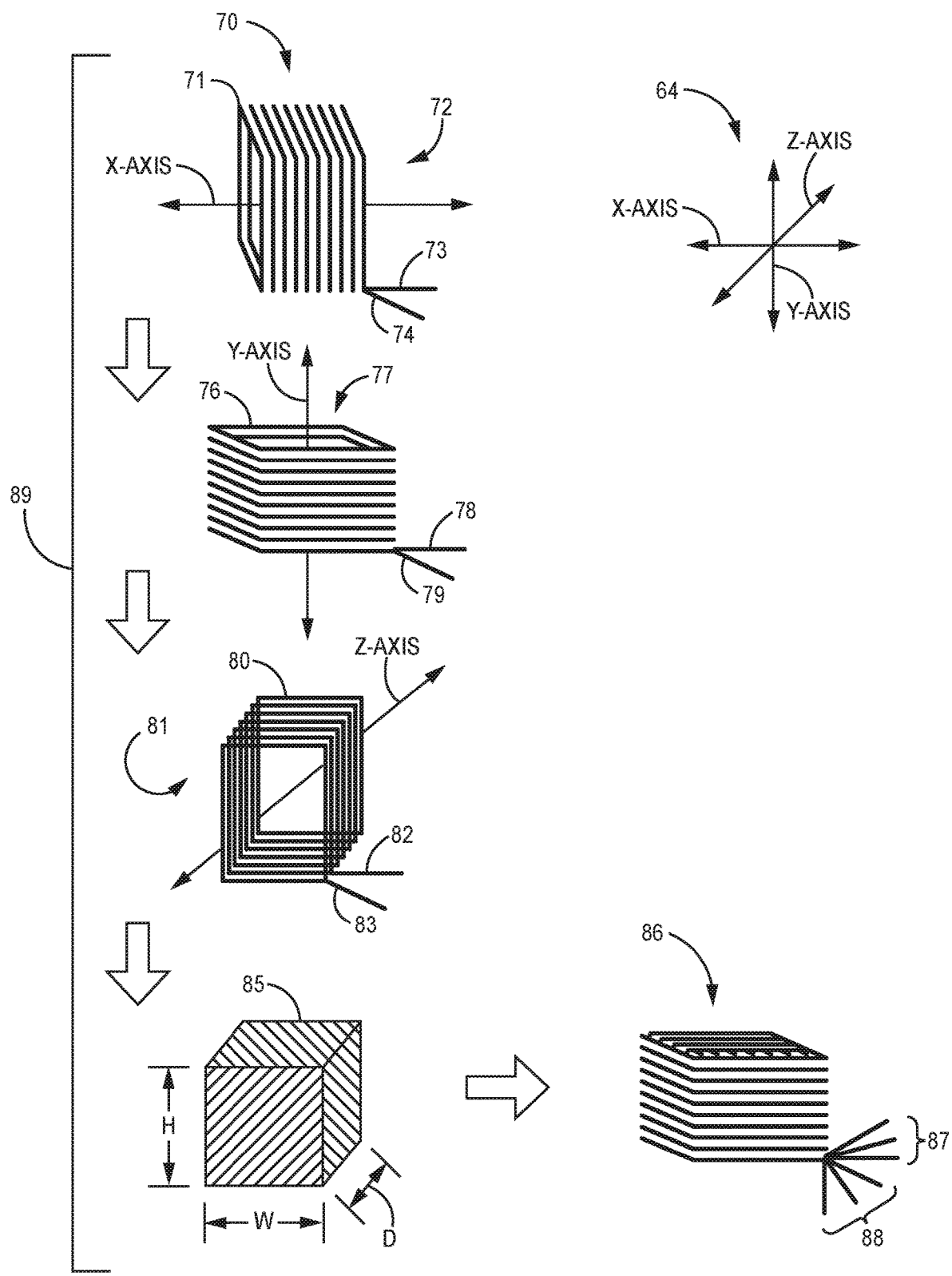
FIG. 4 is an exploded view and an assembled view of a multi-axis antenna according to various examples described in this disclosure.

FIG. 4 illustrates an exploded view 70 and an assembled view 86 of a multi-axis antenna 89 according to various examples described in this disclosure. The multi-axis antenna 89 as shown in FIG. 4 may be the multi-axis antenna of any of IMD 15A, IMD 15B, and sensor circuits 18 as illustrated and described with respect to FIG. 1, and/or the multi-axis antenna 40 of device 30 as illustrated and described with respect to FIG. 2. The multi-axis antenna 89 as shown in FIG. 4 may be configured as antenna 63, and coupled to one or more additional electrical devices, as illustrated and described with respect to FIG. 3.

Referring again to FIG. 4, antenna 89 includes a first coil 71, which may be referred to as the X-axis coil, a second coil 76, which may be referred to as the Y-axis coil, and a third coil 80, which may be referred to as the Z-axis coil. Each of coils 71, 76, and 80 may be configured so that each of the windings forming the coils, respectively, may be positioned relative to a ferrite core 85 so that the windings encircle a portion of the ferrite core 85, and in some examples may encircle a portion of one or two of the other coils. For example, first coil 71 may be formed as winding of an electrical conductor, such as a wire formed of an electrically conductive material such as copper. The electrical conductor forming first coil 71 may include a first terminal 73 coupled to a first end of the winding, and a second terminal 74 coupled to a second end of the winding opposite the first end of the winding. The first terminal 73 and the second terminal 74 are arranged to allow the winding forming first coil 71 to be coupled to additional electrical devices and/or circuitry, such as one or more tuning/smoothing capacitors, a diode, and/or recharging circuitry configured to direct and control a current induced into first coil 71 to allow the induced current to be utilized in recharging a rechargeable power source of an implanted medical device.

As illustrated in FIG. 4, first coil 71 is formed of a winding that encircles a portion of the X-axis of the three-axis coordinate system 64, and thus may be referred to as the X-axis coil. The winding forming first coil 71 includes an interior space 72 comprising an opening in the winding that extends through the winding forming first coil 71 along the X-axis, and providing the interior shape of first coil 71 in cross-section that is perpendicular to the X-axis. The interior space 72 of first coil 71 may comprise an interior shape, such as a square cubic shape, that corresponds to a shape of ferrite core 85 at least with respect to the sides of ferrite core 85 in cross-section relative to the height "H" dimension and the depth "D" dimension of ferrite core 85. The dimensions of the interior space 72 of first coil 71 are at least large enough to allow first coil 71 to be positioned so that first coil 71 encircles at least a portion of the ferrite core 85 around a height and depth dimension of the ferrite core 85. In some examples, the dimensions of interior space 72 are large enough to allow one or more of the windings of second coil 76 and/or third coil 80 to be at least partially positioned within interior space 72 and having the winding forming first coil 71 encircle at least a portion of the second coil 76 and/or the third coil 80 while also encircling a portion of the ferrite core 85. In other examples, the dimensions of interior space 72 of first coil 71 are such that the interior space is just sufficiently large enough to encircle the exterior dimensions of core 85.

Similarly, second coil 76 may be formed as winding of an electrical conductor, such as a wire formed of an electrically conductive material such as copper. The electrical conductor forming second coil 76 may include a first terminal 78 coupled to a first end of the winding, and a second terminal 79 coupled to a second end of the winding opposite the first end of the winding. The first terminal 78 and the second terminal 79 are arranged to allow the winding forming second coil 76 to be coupled to additional electrical devices and/or circuitry, such as one or more tuning/smoothing capacitors, a diode, and/or recharging circuitry configured to direct and control a current induced into second coil 76 to allow the induced current to be utilized in recharging a rechargeable power source of an implanted device.

As illustrated in FIG. 4, second coil 76 is formed of a winding that encircles a portion of the Y-axis of the three-axis coordinate system 64, and thus may be referred to as the Y-axis coil. The winding forming second coil 76 includes an interior space 77 comprising an opening in the winding that extends through the winding forming second coil 76 along the Y-axis, and providing an interior shape of second coil 76 in cross-section that is perpendicular to the Y-axis. The interior space 77 formed by second coil 76 may include a shape, such as a square cubic shape, that corresponds to a shape of ferrite core 85 at least with respect to the sides of ferrite core 85 in cross-section relative to the width "W" dimension and the depth "D" dimension of ferrite core 85. The dimensions of the interior space 77 of second coil 76 are at least large enough to allow second coil 76 to be positioned so that second coil 76 encircles at least a portion of the ferrite core 85 around a width and a depth dimension of the ferrite core 85. In some examples, the dimensions of interior space 77 is large enough to allow one or more of the windings of first coil 71 and/or third coil 80 to be at least partially positioned within interior space 77 and having the winding forming second coil 76 encircle at least a portion of the first coil 71 and/or the third coil 80 while also encircling a portion of the ferrite core 85. In other examples, the dimensions of interior space 77 of second coil 76 are such that the interior space is just sufficiently large enough to encircle the exterior dimensions of core 85.

Third coil 80 of antenna 89 may be formed as winding of an electrical conductor, such as a wire formed of an electrically conductive material such as copper. The electrical conductor forming third coil 80 may include a first terminal 82 coupled to a first end of the winding, and a second terminal 83 coupled to a second end of the winding opposite the first end of the winding. The first terminal 82 and the second terminal 83 are arranged to allow the winding forming third coil 80 to be coupled to additional electrical devices and/or circuitry, such as one or more tuning/smoothing capacitors, a diode, and/or recharging circuitry configured to direct and control a current induced into third coil 80 to allow the induced current to be utilized in recharging a rechargeable power source of an implanted device.

As illustrated in FIG. 4, third coil 80 is formed of a winding that encircles a portion of the Z-axis of the three-axis coordinate system 64, and thus may be referred to as the Z-axis coil. The winding forming third coil 80 includes interior space 81 comprising an opening in the winding that extends through the winding forming third coil 80 along the Z-axis, and providing an interior shape of third coil 80 in cross-section that is perpendicular to the Z-axis. The interior space 81 of third coil 80 may comprise a shape, such as a square shape, that corresponds to a shape of ferrite core 85 at least with respect to the sides of ferrite core 85 in cross-section relative to the height "H" dimension and the width "W" dimension of ferrite core 85. The dimensions of the interior space 81 of third coil 80 are at least large enough to allow third coil 80 to be positioned so that third coil 80 encircles at least a portion of the ferrite core 85 around a height and a width dimension of the ferrite core 85. In some examples, the dimensions of interior space 81 are large enough to allow one or more of the windings of first coil 71 and/or second coil 76 to be at least partially positioned within interior space 81 and having the winding forming third coil 80 encircle at least a portion of the first coil 71 and/or the second coil 80 while also encircling a portion of the ferrite core 85. In other examples, the dimensions of interior space 81 of third coil 80 are such that the interior space is just sufficiently large enough to encircle the exterior dimensions of core 85.

Assembled view 86 illustrates an example of multi-axis antenna 89 assembled to include first coil 71, second coil 76, and third coil 80, each coil positioned to encircle some portion of ferrite core 85, and wherein portions of at least two of the coils are at least partially encircled by one of the coils. As illustrated by assembly view 86, the first coil 71 is positioned around the core 85, and having the winding forming first coil 71 in contact with exterior surfaces of core 85 forming the height "H" and the depth "D" dimension of the core. The third coil 80 is positioned around the core 85 and encircling at least a portion of the winding forming first coil 71. The second coil 76 is positioned around the core 85 and encircling at least a portion of the winding forming first coil 71 and at least a portion of winding forming third coil 80. When assembled as shown in assembly view 86, core 85 may be included, at least partially within interior space 72 of first coil 71, wherein core 85 and first coil 71 may be included, at least partially, within interior space 81 of third coil 80, and wherein core 85, first coil 71, and third coil 80 may be included, at least partially, within interior space 77 of second coil 76.

When assembled as shown in assembly view 86, at least one coil of first coil 71, second coil 76, and third coil 80 has an axis of orientation that corresponds with one of the X-axis, the Y-axis, and the Z-axis, respectively, of the three-axis coordinate system 64. As such, any angle of orientation of a magnetic field that may be imposed upon the assembled antenna 89 may induce a current in at least one of the coils forming antenna 89, and for example when coupled as a receive antenna in an implantable medical device. As such, any orientation of the multi-axis antenna 89 being configured to have currents induced in the coils of the antenna relative to an externally generated magnetic field or magnetic fields imposed on the antenna may generate a current in at least one of coils 71, 76, and/or 80 regardless of the orientation of the direction of the magnetic field relative to the orientation of the antenna 89. These induced current or currents may be applied to a rechargeable power source coupled to the antenna 89 for the purpose of recharging the power source. As described, these induced currents may be provided by antenna 89 irrelevant of the orientation of the direction of the magnetic field or magnetic fields impose on the antenna 89 because of the orthogonal arrangement of the orientations of the three coils of the antenna 89 relative to each other.

The order in which the assembly of the coils 71, 76, and 80 is provided relative to the core 85, e.g., the layering of the coils relative to one another, is not limited to any particular arrangement or to any particular order. For example, any one of coils 71, 76, or 80 may be positioned in assembly view 86 as closest to core 85, with the remaining coils positioned in any order so that the coil positioned closest to core 85 in included, at least partially within the interior space of the remaining two coils. The coil of coils 71, 76, and 80 that is positioned as the outermost layer of assembly view 86 may be configured so that a least a part of core 85 and the two additional coils are positioned, at least partially, within the interior space of the outer most coil.

As shown in the assembly view 86, a first set of terminals terminal of each of first coil 71, second coil 76, and third coil 80 (e.g., first terminals 73, 78, and 82) may extend from a common point, e.g., from a position proximate to a same corner of core 85, illustrated in FIG. 4 as leads 87. In addition, a second set of terminals of each of first coil 71, second coil 76, and third coil 80 (e.g., second terminals 74, 79, and 83) may extend from a common point, e.g., from a position proximate a same corner of core 85 illustrated in FIG. 4 as leads 88. Leads 87 may extend from a same corner of assembly view 86 as a corner proximate to leads 88, or leads 87 may extend from a first corner of assembly view 86, and leads 88 may extend from a second and different corner of assembly view 86. Having leads 87 and 88 extend from a same corner, or having lead 87 extend together from a first corner and having lead 88 extend from a second different corner, may allow connection of these leads to additional electronic devices and/or electrical circuitry to be made using less space and/or less additional conductive leads within the implantable medical device, and thus further the advantages obtained by use of the multi-axis antenna 89. For example, one set of leads 87 or 88 may all be coupled to a common point, such as common voltage node 68 illustrated in schematic diagram 50 in FIG. 3. As illustrated in FIG. 4, having at least one set of leads 87 or 88 exit assembly view 86 of the antenna at a common point may therefore reduce the number of individual conductors that may need to extend within the device where antenna 89 is located, and thus help further minimum the amount of space, and thus in some examples the overall size of the device.

As illustrated in FIG. 4, the height "H" dimension, the width "W" dimension, and the depth "D" dimension of ferrite core 85 may be equal in value so that core 85 forms a cubic volume. In some examples, the value for each of the height, width, and depth dimensions of core 85 are each three millimeters (mm), providing an overall volume for core 85 of twenty-seven cubic millimeters (mm³). However, the value for the dimension for any give one of the height, width, and depth dimension are not limited to having a same value, and may have different values that render the overall shape of ferrite core 85 to some shape other than a cube. For example, the ferrite core 85 may provide a spherical shaped outer surface over which the coil or coils forming the multi-axis antenna are positioned. In other examples, ferrite core 85 may be provided in the shape of an upright cylinder, having a square, circular, or elliptical shape in cross-section. Further, the material used to form core 85 is not limited to a particular type of material, and in some examples, is a ferrite material comprising a compound that includes iron oxides, and may be combined with nickel, zinc, and or manganese compounds. The ferrite material used to form core 85 may include "soft ferrites" that have low coercivity (magnetization in the material can be easily revered in direction without generated large levels of hysteresis losses) and having high resistivity, which helps reduce eddy current flowing in the material.

The electrical conductor used to form the windings of first coil 71, second coil 76, and third coil 80 are not limited to being formed from any particular type of material, and may be formed from a conductive metal, such as copper, that is easily formed into a wire and may be easily bent to form the desired shape of the winding for each of the coils. The electrical conductors in some examples may include an insulative material, such as enamel, coated over the exterior surface of the conductor to provide an insulative layer between the individual windings of a single one of the coils, and also between winding of different coils that may be brought into contact with one another as part of the assembly used to form antenna 89. In various examples, the electrical conductor used to form the windings of each coil is Litz wire, for example a single or multiple stranded wire, wherein the electrical conductor used to form each winding is insulated along the outer surface of the electrical conductor, for example using a coating, such as enamel, to reduce the skin effect of the electrical conductor. Skin effect is the characteristic of electrical current flowing through an electrical conductor that causes the flow of current in the electrical conductor to travel though the outer portion, e.g., the "skin" of the conductor, and not through the inner portion of the electrical conductor. The skin effect is more pronounced at higher frequencies. The use of Litz wire helps reduce the skin effect in the electrical conductor at higher frequencies.

In addition, the inter-turn capacitance of the respective windings/turns is reduced by increasing inter-turn distances, thus increasing the self-resonant frequency of the assembly and enabling higher modulation frequency to be applied to the coil. In addition, the overall shape of a coil formed to encircle a portion of ferrite core 85 may not encircle an interior space within the coil itself that conforms to the shape of the portion of the ferrite core 85 encircled by the coil. For example, the windings of the coil may extend outward away from certain portions of the surface of the ferrite core 85 while contacting other portions of the ferrite core, so the that the shape of the interior portion of the coil does not correspond exactly to the shape of the exterior portion of the ferrite core 85 that the coil encircles. In one example, the ferrite core may be cubic in shape, while the windings forming the coils encircling the ferrite core may be shaped more like a rounded-corner square with sides of the square shape that are arc-shaped rather than being linear, the arc-shaded sided extending outward from a center point of the interior space encircled by the coil winding between the corners of the rounded-corner square.

In one specific example, each of the first coil 71, second coil 76, and third coil 80 comprise a winding respectively formed with 10/46 Litz wire, using 10 turns of wire per coil and the winding formed on a 3 mm by 3 mm by 3 mm ferrite cube. Using an antenna having coils wound in this manner, a 20 milliampere-hour (mAh) rechargeable battery implanted at a depth of approximately 15 centimeters within a body of a patient may be recharged in approximately sixty minutes. In some examples, the 20 mAh battery may be expected to be able to provide power to an implanted medical device, such as device 30 as illustrated and describe with respect to FIG. 2 for a period of at least one year. As such, the need to perform a recharging process on a power source of an implanted medical device may be minimized, for example to a period of approximately one hour, and thus reduce the cost, inconvenience and the need for repeated visits for example to a clinic or hospital in order to maintain a proper power for an implanted medical device. Further the time to recharge the implanted medical device using the multi-axis antenna may be relatively fast. For example, using the multi-axis antenna described in this paragraph, an 18 mAh battery may be charged from 0.38 volts to a voltage level of 2.6 volts in approximately 30 minutes with any random orientation between the magnetic field imposed on the implanted device at a depth of 15 centimeters for implantation while maintaining acceptable levels of electromagnetic exposure for the patient. Examples of batteries that may be charged using the multi-axis antenna described in this paragraph are not limited to these mAh or voltage ratings, and for example may include batteries having larger or smaller mAh ratings, and other voltage ranges, such as 0.0 to 4.5 volts.

Examples of antenna 89 are described as comprising a ferrite core 85. However, examples of antenna 89 may also comprise coils 71, 76, and 80 having orthogonal axis of orientation and assembled as illustrated and described above as shown in assembly view 86, but without the ferrite core 85. In some examples, the assembly of coils 71, 76, and 80 may be formed on a core formed of a non-ferrite material, such as a non-conductive plastic. In some examples, the assembly of coils 71, 76, and 80 may be formed without use of a core of any type, and thus having the interior space of assembly formed as an opening or hollow space.

Further, the use of the multi-axis antenna that is not orientation specific with respect to the orientation of the receive antenna within the implanted medical device and the direction of the magnetic field being imposed on the implanted device to recharge the device may eliminate the need for, and thus reduce the cost associated with, equipment and methods required to align the magnetic fields with a particular orientation of an antenna. In some examples, a single recharging coil, such as a spiral wound planar coil, or a single pair of recharging coils (for example arranged as a Helmholtz coil), may be all that is required for use as the recharging coil or coils providing the magnetic field used to induce currents into the receive antenna of the implanted medical device while providing at least a minimum level of induced currents for a given magnetic field strength regardless of the relative orientation of the imposed magnetic field relative to the orientation of the implanted device.

Figure 5:
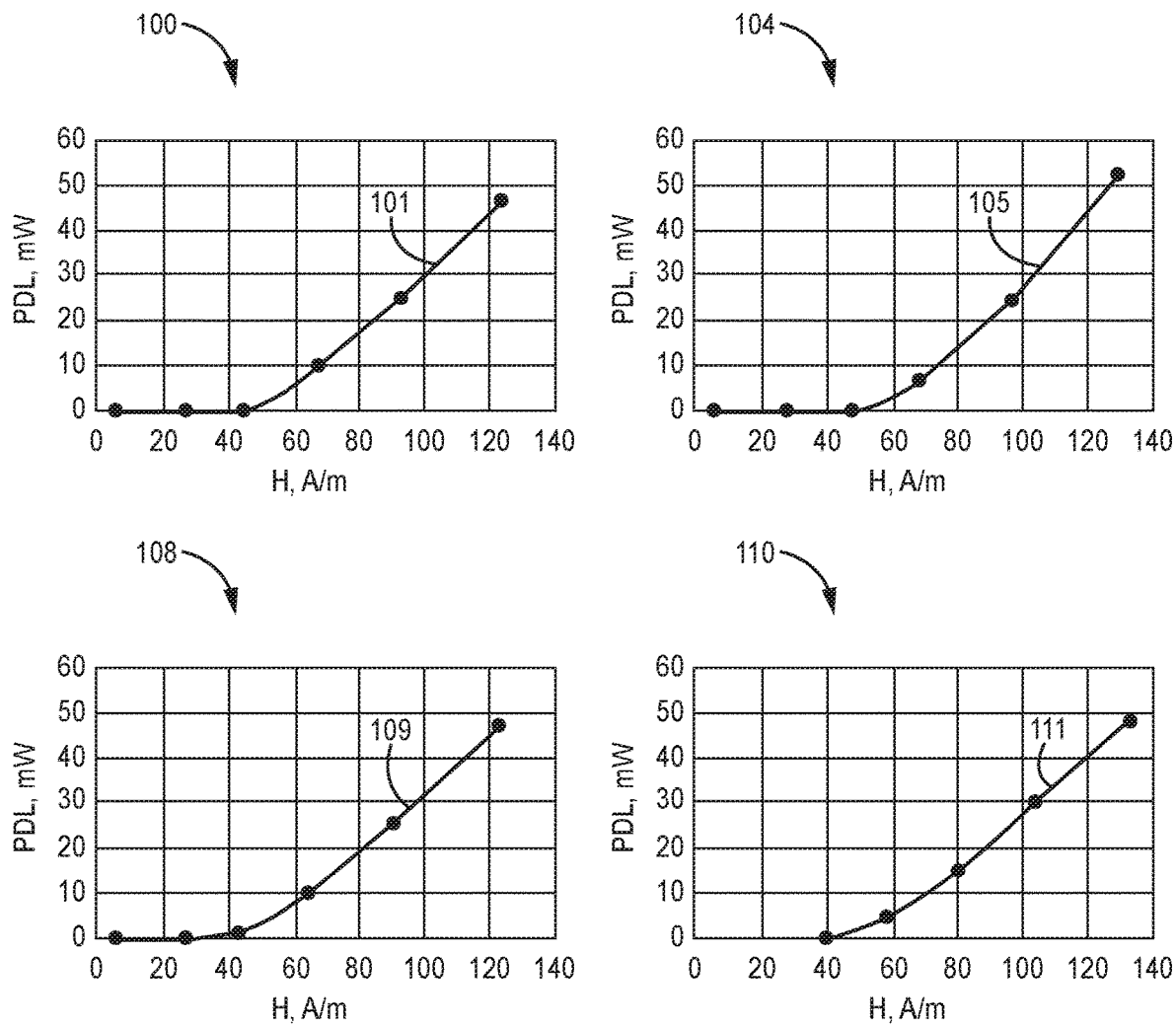
FIG. 5 illustrates a set of graphical diagrams of magnetic field intensities versus induced power as provided by individual coils and a combination of coils of a multi-axis antenna according to various examples described in this disclosure.

FIG. 5 illustrates a set of graphical diagrams 100, 104, 108, and 110, of imposed magnetic field intensities versus induced power as provided by individual coils and a combination of coils of a multi-axis antenna according to various examples described in this disclosure. Graphical diagram 100 is illustrative of an example of resulting power levels delivered to a load, (e.g., a battery of an implanted medical device), as represented by curve 101, for different magnetic field intensities generated by a sinusoidal current applied to a transmit coil and imposed at a predefined distance from the transmit coil onto a first coil of a multi-axis antenna of an implantable medical device. Graphical diagram 100 includes an X-axis representing levels of magnetic field intensity "H" measured in amperes per meter (A/m) at the first coil of the multi-axis antenna. The vertical axis of graphical diagram 100 represents of the resultant power delivered to the load (PDL), in milliwatts (mW), the load representative in some example of the battery of the implanted medical device that is being recharged. Curve 101 represents measured resultant power induced into an example of an X-axis coil of a multi-axis antenna as described for example with respect to FIG. 4. Referring again to FIG. 5, when measuring the resultant power, the first coil was located at a distance of 15 centimeters from the transmit coil generating the magnetic fields, the distance representative of a possible location within a patient for a deeply implanted medical device. For the measurements of the induced power levels illustrated as curve 101, the direction of the magnetic field imposed on the first coil (the X-axis coil) of the multi-axis antenna corresponds to the direction, e.g., was colinear with, the orientation of the X-axis coil. Having the direction of the magnetic field corresponding with the direction of orientation of the X-axis coil, (e.g., magnetic field direction was the same orientation as the normal axis of orientation of the X-axis coil), should provide a maximum level of coupling efficiency between the magnetic field and the X-axis coil, and thus generate the highest level of power induced into the X-axis coil for the given level of magnetic field intensity imposed onto the multi-axis antenna.

Graphical diagram 104 is illustrative of an example of resulting power levels delivered to a load, (e.g., a battery of an implanted medical device), as represented by curve 105, for different magnetic field intensities generated by a sinusoidal current applied to a transmit coil and imposed at a predefined distance from the transmit coil onto a second coil of the receive antenna of same implantable medical device used to generate the data illustrated in graphical diagram 100. Graphical diagram 104 includes an X-axis representing levels of magnetic field intensity "H" measured in amperes per meter (A/m) at the second coil of the multi-axis antenna. The vertical axis of graphical diagram 104 represents of the resultant power delivered to the load (PDL), in milliwatts (mW), the load representative in some examples of the battery of the implanted medical device that is being recharged. Curve 105 represents measured resultant power induced into an example of a Y-axis coil of a multi-axis antenna as described with respect to FIG. 4. Referring again to FIG. 5, when measuring the resultant power, the second coil was located at the same 15 centimeters distance from the transmit coil generating the magnetic fields as was used when measuring the power delivered to the load in graphical diagram 100. For the measurements of the induced power levels illustrated by curve 105 of graphical diagram 104, the direction of the magnetic field imposed on the second coil (the Y-axis coil) of the multi-axis antenna corresponds to the direction, e.g., was colinear with, the orientation of the Y-axis coil. Having the direction of the magnetic field corresponding with the direction of orientation of the Y-axis coil, (e.g., magnetic field direction was the same orientation as the normal axis of orientation of the Y-axis coil), should provide a maximum level of coupling efficiency between the magnetic field and the Y-axis coil, and thus generate the highest level of power induced into the Y-axis coil for the given level of magnetic field intensity imposed onto the multi-axis antenna.

Graphical diagram 108 is illustrative of an example of resulting power levels delivered to a load, (e.g., a battery of an implanted medical device), as represented by curve 109, for different magnetic field intensities generated by a sinusoidal current applied to a transmit coil and imposed at a predefined distance from the transmit coil onto a third coil of the receive antenna of same implantable medical device used to generate the data illustrated in graphical diagrams 100 and 104. Graphical diagram 108 includes an X-axis representing levels of magnetic field intensity "H" measured in amperes per meter (A/m) at the third coil of the multi-axis antenna. The vertical axis of graphical diagram 108 represents of the resultant power delivered to the load (PDL), in milliwatts (mW), the load representative in some examples of the battery of the implanted medical device that is being recharged. Curve 109 represents measured resultant power induced into an example of a Z-axis coil of a multi-axis antenna as described with respect to FIG. 4. Referring again to FIG. 5, when measuring the resultant power, the third coil was located at the same 15 centimeters distance from the transmit coil generating the magnetic fields as was used when measuring the power delivered to the load in graphical diagrams 100 and 104. For the measurements of the induced power levels illustrated by curve 109 of graphical diagram 108, the direction of the magnetic field imposed on the third coil (the Z-axis coil) of the multi-axis antenna corresponds to the direction, e.g., was colinear with, the orientation of the Z-axis coil. Having the direction of the magnetic field corresponding with the direction of orientation of the Z-axis coil, (e.g., magnetic field direction was the same orientation as the normal axis of orientation of the Z-axis coil), should provide a maximum level of coupling efficiency between the magnetic field and the Z-axis coil, and thus generate the highest level of power induced into the Z-axis coil for the given level of magnetic field intensity imposed onto the multi-axis antenna.

For each of graphical diagrams 100, 104, and 108, a resultant power level applied to the load remains at zero mW or nearly zero mW of power for any applied level of magnetic field intensities up to approximately 40 A/m. This is due to the fact that a minimum level of magnetic field intensity must be applied to any given one of the first, second, or third coils of the multi-axis antenna in order to generate a voltage level at the coil that is adequate to overcome the forward biasing voltage level for the individual diode coupled in series with that particular coil. Once a voltage that is adequate to overcome the biasing voltage of the diode associated with a given coil has been generated within that coil of the multi-axis antenna, that coil will begin to provide a current flow, and thus begin to deliver power to the load.

For example, when a magnetic field intensity in excess of 40 A/m is applied to the first coil, the level of power delivered to the load by the first coil begins to increase from a non-zero value in some relationship based on the level of the applied magnetic field intensity, as indicated by curve 101. As shown by curve 101, the power delivered to the load by the first coil exceeds 40 mW when a magnetic field intensity of 120 A/m is imposed on the first coil, as illustrated by graphical diagram 100. When a magnetic field intensity in excess of 40 A/m is applied to the second coil, the level of power delivered to the load by the second coil begins to increase from a non-zero value in some relationship based on the level of the applied magnetic field intensity, as indicated by curve 105. As shown by curve 105, the power delivered to the load by the second coil exceeds 40 mW when a magnetic field intensity of 120 A/m is imposed on the second coil, as illustrated by graphical diagram 104. When a magnetic field intensity in excess of 40 A/m is applied to the third coil, the level of power delivered to the load by the third coil begins to increase from a non-zero value in some relationship based on the level of the applied magnetic field intensity, as indicated by curve 109. As shown by curve 109, the power delivered to the load by the third coil exceeds 40 mW when a magnetic field intensity of 120 A/m is imposed on the third coil, as illustrated by graphical diagram 108.

Each of graphical diagrams 100, 104, and 108 illustrate curves representative of measured resultant power levels induced into the first, second, and third coils, respectively, of a multi-axis antenna wherein for each diagram, the magnetic field imposed on each coil, respectively, was oriented to have a direction that corresponds to the axis of orientation (normal axis) for the coil being measured for induced power levels. Graphical diagram 110 is illustrative of an example of resultant power levels delivered to a load, (e.g., a battery of an implanted medical device), as represented by curve 111, for different magnetic field intensities generated by a sinusoidal current applied to a transmit coil and imposed at the predefined distance from the transmit coil onto each of the three coils of a multi-axis antenna of the same implantable medical device used to generate the data illustrated in graphical diagrams 100, 104, and 108. When imposing the magnetic fields onto the multi-axis antenna to measure power levels delivered by all three of the coils of the multi-axis antenna combined, the direction of the magnetic field was random, and did not necessarily align with any axis of orientation (e.g., a normal axis of orientation) for any of the first, second, or third coils of the multi-axis antenna.

Graphical diagram 110 includes an X-axis representing levels of magnetic field intensity "H" measured in amperes per meter (A/m) at the multi-axis antenna. The vertical axis of graphical diagram 110 represents of the resultant power delivered to the load (PDL), in milliwatts (mW), the load representative in some examples of the battery of the implanted medical device that is being recharged. Curve 1111 represents measured resultant power induced into an example of the multi-axis antenna as described with respect to FIG. 4. Referring again to FIG. 5, when measuring the resultant power, the multi-axis antenna was located at the same 15 centimeters distance from the transmit coil generating the magnetic fields as was used when measuring the power delivered to the load in graphical diagrams 100, 104, and 108. The levels of power delivered to the load as illustrated by curve 111 in graphical diagram 110 indicate a combined level of power delivered by the three coils of the multi-axis antenna, but wherein the direction of the magnetic field imposed onto the multi-axis antenna had a random orientation relative to the orientation of the three coils and the multi-axis antenna.

As illustrated by graphical diagram 110, a level of power delivered to the load by the multi-axis antenna includes power levels at any given level of imposed magnetic field intensity that are similar in magnitude to the levels of power provided by any one of the individual coils as indicated in graphical diagrams 100, 104, and 108 for a same level of magnetic field intensity. However, a random orientation of the magnetic field direction of the imposed magnetic fields was applied to the multi-axis antenna when measuring the PDL level indicated by curve 111. When applying the magnetic fields having the random orientation for the magnetic field direction to all three of the coils of the multi-axis antenna, the resultant power level applied to the load remained at a zero mW, or at nearly zero mW levels of power for any applied magnetic field intensities up to approximately 40 A/m. When the level of the imposed magnetic field intensity exceeded 40 A/m, and still having the random direction of orientation relative to the multi-axis antenna, the level of power delivered to the load by the multi-axis antenna begins to increase from the non-zero value in some relationship based on the level of the applied magnetic field intensity, as indicated by curve 111. As shown by curve 111, the power delivered to the load by the multi-axis antenna follows a curve 111 corresponding to the curves 101, 105 and 109 of the individual coils of the antenna, and for example provides approximately 40 mW of power to the load when a magnetic field intensity of 120 A/m is imposed on the multi-axis antenna, as illustrated in graphical diagram 110.

The measured values for PDL as illustrated by graphical diagrams 110, 104, 108, and 110 demonstrate that the multi-axis antenna may deliver a similar level of power to a load for a given level of magnetic field intensity imposed on the coils of the multi-axis antenna, but with a random orientation of the antenna relative to a direction of the imposed magnetic field compared to a "best scenario" alignment of the direction of the imposed magnetic field relative to a given coil of the antenna. As such, the performance of the multi-axis antenna can be the same or comparable to a planar or single-axis antenna when a magnetic field fully aligned with the axis of the planar or signal axis antenna is used to induce power into the planar or single-axis antenna, but without the need for alignment of the direction of the magnetic field being imposed onto the multi-axis antenna with an axis of orientation of any of the coils forming the multi-axis antenna. This feature of not requiring an alignment in order to induce a level of power into the multi-axis antenna may provide the benefit of allowing a minimum level of inductive coupling to be obtained between a transmit coil and the multi-axis antenna of an implanted device without the need for an elaborate alignment procedure to be performed, and/or without the need for additional equipment needed to position and align the transmit coil. The advantages of the lack of need for alignment of the transmit coil may be particularly beneficial for recharging devices that may be implanted within a location a ventricle of a heart of a patient, such as device 30 as illustrated and described with respect to FIG. 2. These types of implants may allow the device to move to some degree after being implanted, for example in response to heartbeats of the patient. As such, maintaining continuous alignment of the direction of a magnetic field generated by a transmit coil to an axis of orientation of a planar or single axis antenna of an implanted device may be difficult or impossible due to the continued movement of the device. The ability to achieve a same and minimum level of inductive coupling between a transmit coil providing a magnetic field being imposed onto the multi-axis antenna of a device that may be moving may provide an additional benefit of efficient recharging of these type devices compared to similar device that may comprise a planar or single axis receive antenna within or coupled to the device to be recharged.

Figure 6:
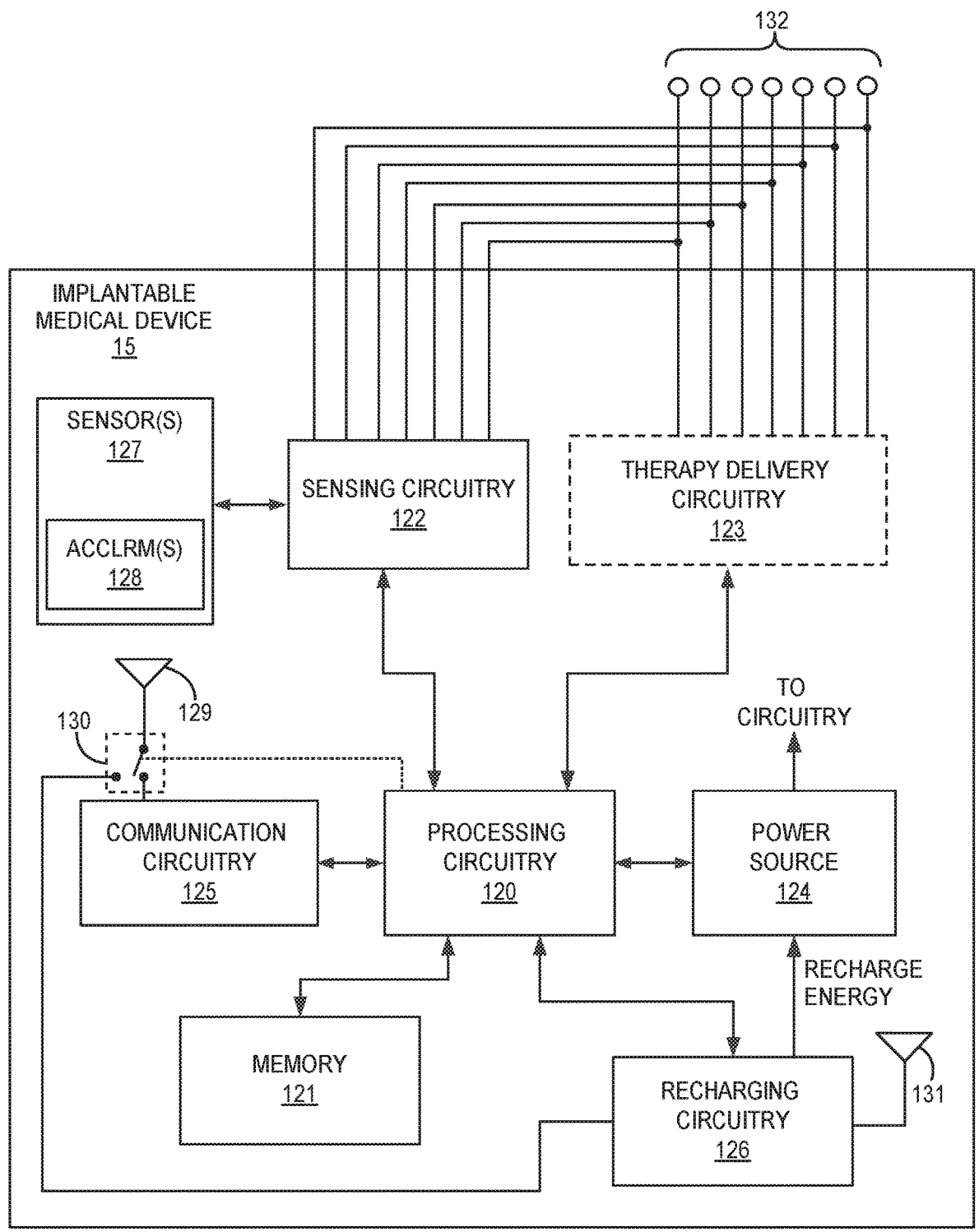
FIG. 6 is a functional block diagram of an intracardiac pacing device according to various examples described in this disclosure.

FIG. 6 is a functional block diagram illustrating an example configuration of an IMD 15 according to various examples described in this disclosure. IMD 15 may correspond to any of IMD 15A and IMD 15B described and illustrated with respect to FIG. 1 and/or device 30 as described and illustrated with respect to FIG. 2, or another IMD configured to be rechargeable using the devices, systems, and methods as described in this disclosure. IMD 15 includes a power source 124 that may be coupled to the electronic circuitry provided in IMD 15, and is configured to provide electrical power to these circuits. IMD 15 may be inductively rechargeable by imposing one or more magnetic fields onto IMD 15, wherein energy from these imposed field(s) may induce an electrical energy into antenna 129 coupled to communication circuitry 125 and to device recharging circuitry 126, or into an antenna 131 that may be provided in addition to antenna 129 and that when provided, is also coupled to recharging circuitry 126. When configured to be used for recharging IMD 15, antenna 129 and/or antenna 131 may be a multi-axis antenna according to any of the examples of multi-axis antennas described in this disclosure, or any equivalents thereof. IMD 15 may be an example of a deeply implanted device, such as a device implanted within a chamber of the heart of a patient, and including a multi-axis antenna as described in this disclosure that allows efficient recharging of a power source (e.g., power source 124) located within the IMD using a random orientation of a magnetic field imposed on the IMD to recharge the power source.

As shown in FIG. 6, device recharging circuitry 126 is coupled to power source 124, and may be coupled through switching device 130 to receive electrical energy induced in antenna 129 (or in antenna 131 when provided) by one or more electromagnetic fields imposed on the antenna, and to regulate the energy to provide a level of energy that is provided to power source 124 for the purpose of recharging power source 124 and/or powering the other circuitry included as part of IMD 15. Device recharging circuitry 126 may perform various energy conditioning functions to the energy inductively generated in antenna 129 (or antenna 131 when provided), for example by providing rectification, voltage level regulation, current level regulation, and/or other signal processing functions in order to generate the "recharging energy" provided to power source 124. Antenna 129 (and/or antenna 131 when provided) may be a multi-axis antenna that is not orientation specific with respect to the coupling efficiency of the inductive charging of power source 124 based on the orientation of the antenna relative to the orientation of the coil or coils providing the magnetic field(s) intended to recharge power source 124.

Thus, IMD 15 may be configured to couple magnetic energy captured by an antenna (including, but not necessarily a telemetry antenna), directed into a suitable rectifying circuit that delivers the electrical energy to an energy storage device such as a rechargeable battery. The switching device 130, which may be a transistor, may be included in IMD 15 and may be controlled, for example by processing circuitry 120, to select whether the telemetry or the power recharge system is active, and thus whether multi-axis antenna 129 is coupled to the communication circuitry 125 or the device recharging circuitry 126. In other examples, the second antenna 131 is coupled directly to device recharging circuitry 126, and is configured to receive the inductively coupled energy provided to antenna 131, and to provide the inductively coupled energy to device recharging circuit 126 to recharge power source 124.

In the illustrated example, IMD 15 includes processing circuitry 120 and an associated memory 121, sensing circuitry 122, therapy delivery circuitry 123, one or more sensors 127, and the communication circuitry 125 coupled to antenna 129 as describe above. However, IMD 15 need not include all of these components, or may include additional components. For example, IMD 15 may not include therapy delivery circuitry 123 in some examples of the device. Memory 121 includes computer-readable instructions that, when executed by processing circuitry 120, causes IMD 15 and processing circuitry 120 to perform various functions attributed to IMD 15 and processing circuitry 120 as described herein (e.g., preparing information for transmission from IMD 15 regarding a level of charge present in a power source, such as a battery management system information (BMS)). For example, processing circuitry 120 may be configured to provide information including a state of charge, and/or temperature information related to a battery, e.g., a battery located in IMD 15, determining a level of inductive coupling, e.g., energy level being generated in an antenna located in IMD 15 as a result of an electromagnetic field or fields being imposed on IMD 15, and generate information related to this inductively received energy for transmission by the communication antenna or separate antenna and associated power conditioning circuitry of IMD 15.

Memory 121 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 121 may store threshold(s) for time of day, posture, heart rate, activity level, respiration rate, and other parameters. Memory 121 may also store data indicating cardiovascular pressure measurements, and store other data associated with cardiac and/or other physiological events associated with a patient.

Processing circuitry 120 may include fixed function circuitry and/or programmable processing circuitry. Processing circuitry 120 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 120 may include multiple components, such as any combination of one or more microprocessors, one or more controllers, one or more DSPs, one or more ASICs, or one or more FPGAs, as well as other discrete or integrated logic circuitry. The functions attributed to processing circuitry 120 herein may be embodied as software, firmware, hardware or any combination thereof.

As illustrated, sensing circuitry 122 and therapy delivery circuitry 123 are coupled to electrodes 132. Electrodes 132 as illustrated in FIG. 6 may correspond to, for example, electrodes located on leads 21 and 22 and/or the housing 23 of IMD 15A (FIG. 1), or electrodes 32 and 33 of device 30 (FIG. 2). Sensing circuitry 122 in IMD 15 as shown in FIG. 6 may monitor signals from a selected two or more of electrodes 132 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 122 may include one or more filters and amplifiers for filtering and amplifying a signal received from electrodes 132.

In some examples, sensing circuitry 122 may sense or detect physiological parameters, such as heart rate, blood pressure, respiration, and other physiological parameters associated with a patient. The resulting electrical signals may be passed to cardiac event detection circuitry that detects a cardiac event for example when a cardiac electrical signal crosses a sensing threshold. The cardiac event detection circuitry may include a rectifier, filter and/or amplifier, a sense amplifier, comparator, and/or analog-to-digital converter. Sensing circuitry 122 may output an indication to processing circuitry 120 in response to sensing of a cardiac event (e.g., detected P-waves or R-waves).

In this manner, processing circuitry 120 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P-waves or R-waves, and provide indications of the occurrences of such events to processing circuitry 120, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 122 may also include switching circuitry to select which of the available electrodes 132 (or electrode polarities) are used to sense the heart activity. In examples with several electrodes 132, processing circuitry 120 may select the electrodes that function as sense electrodes, i.e., select the sensing configuration, via the switching circuitry within sensing circuitry 122. Sensing circuitry 122 may also pass one or more digitized EGM signals to processing circuitry 120 for analysis, e.g., for use in cardiac rhythm discrimination.

In the example of FIG. 6, IMD 15 includes one or more sensors 127 coupled to sensing circuitry 122. Although illustrated in FIG. 6 as included within IMD 15, one or more of sensors 127 may be external to IMD 15, e.g., coupled to IMD 15 via one or more leads, or configured to wirelessly communicate with IMD 15. In some examples, sensors 127 transduce a signal indicative of a patient parameter, which may be amplified, filtered, or otherwise processed by sensing circuitry 122. In such examples, processing circuitry 120 determines values of patient parameters based on the signals. In some examples, sensors 127 determine the patient parameter values, and communicate them, e.g., via a wired or wireless connection, to processing circuitry 120.

In some examples, sensors 127 include one or more accelerometers 128, e.g., one or more three-axis accelerometers. Signals generated by the one or more accelerometers 128 may be indicative of, as examples, gross body movement (e.g., activity) of the patient, patient posture, heart sounds or other vibrations or movement associated with the beating of the heart, or coughing, rales, or other respiration abnormalities. Accelerometers 128 may produce and transmit signals to processing circuitry 120 for a determination as to the posture of the patient. In various examples, signals from the accelerometers 128 are processed to determine an activity, such as when the patient is taking a step or steps, or for example when the patient is running, and used to provide an activity count associated with patient initiated physical activity of the patient. In some examples, sensors 127 may include sensors configured to transduce signals indicative of blood flow, oxygen saturation of blood, or patient temperature, and processing circuitry 120 may determine patient parameters values based on these signals. In various examples, sensors 127 may include one or a combination of sensor circuits 18 (FIG. 1) as previously described.

In some examples, processing circuitry 120 determines one or more patient parameter values based on pressure signals. Patient parameter values determined based on pressure may include, as examples, systolic or diastolic pressure values, such as pulmonary artery diastolic pressure values. In some examples, a separate device such as sensor circuits 18 (FIG. 1), include one or more sensors and sensing circuitry configured to generate a pressure signal, and processing circuitry 120 determines patient parameter values related to blood pressure based on information received from IMD 15.

Therapy delivery circuitry 123, when provided as part of IMD 15, may be configured to generate and deliver electrical therapy to the heart. Therapy delivery circuitry 123 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 123 may include a first set of components configured to provide pacing therapy and a second set of components configured to provide anti-tachyarrhythmia shock therapy. In other instances, therapy delivery circuitry 123 may utilize the same set of components to provide both pacing and anti-tachyarrhythmia shock therapy. In still other instances, therapy delivery circuitry 123 may share some of the pacing and shock therapy components while using other components solely for pacing or shock delivery.

Therapy delivery circuitry 123 may include charging circuitry, one or more charge storage devices, such as one or more capacitors, and switching circuitry that controls when the capacitor(s) are discharged to electrodes 132 and the widths of pulses. Charging of capacitors to a programmed pulse amplitude and discharging of the capacitors for a programmed pulse width may be performed by therapy delivery circuitry 123 according to control signals received from processing circuitry 120, which are provided by processing circuitry 120 according to parameters stored in memory 121. Processing circuitry 120 controls therapy delivery circuitry 123 to deliver the generated therapy to the heart via one or more combinations of electrodes 132, e.g., according to parameters stored in memory 121. Therapy delivery circuitry 123 may include switch circuitry to select which of the available electrodes 132 are used to deliver the therapy, e.g., as controlled by processing circuitry 120.

Communication circuitry 125 includes any suitable hardware, firmware, software or any combination thereof for communicating with another device, such as an external device 11, transceiver 16, or another IMD or sensors, such as sensor circuits 18, as shown in FIG. 1 and FIG. 2. Referring again to FIG. 6, under the control of processing circuitry 120, communication circuitry 125 may receive downlink telemetry from and send uplink telemetry to external device 11 or another device with the aid of an antenna, such as antenna 129, which may be internal and/or external. In some examples, communication circuitry 125 may communicate with a local external device, for example through transceiver 16, and processing circuitry 120 may communicate with a networked computing device via the local external device and a computer network, such as the Medtronic® CareLink® Network developed by Medtronic, plc, of Dublin, Ireland.

As described above, in some examples (i.e., where a single antenna is used) the antenna signal can be switched from the telemetry communication circuitry 125 to the recharging circuitry 126. In other examples the recharge antenna/coil is separate from the communication/telemetry antenna. For example, antenna 129 may be switched between being coupled to communication circuitry 125 and device recharging circuitry 126 by switching device 130, wherein switching device 130 may be controlled by processing circuitry 120 to determine when antenna 129 is coupled to the communication circuitry 125 and when antenna 129 is to be coupled to the device recharging circuitry 126.

In various examples, processing circuitry 120 is coupled to device recharging circuitry 126, and receives information, such as a level of current, that is being induced in antenna 129 or antenna 131 as a result of electrical energy received by the antenna via magnetic energy imposed on IMD 15 for the purpose of recharging power source 124. Processing circuitry 120 may provide this and other information, for example charge rate and temperature information associated with the power source 124, in the form of an output signal to communication circuitry 125 for transmission from IMD 15 to one or more external devices, such as transceiver 16. This transmitted information may be used by the external device(s) to control one or more aspects of the recharging process. For example, positioning and/or a level of power being applied to a recharging coil or a pair of coils located externally to IMD 15 and generating the magnetic field or fields being imposed on IMD 15 may be controlled using this information transmitted from IMD 15. The setting of electrical parameters used to energize the coil of the pair of coils generating the magnetic field or fields imposed onto IMD 15 for the purpose of recharging the power source 124 may be controlled using this information transmitted from IMD 15. In addition, other information such as temperature and field intensity information transmitted from IMD 15, may be used to control the recharging process, for example by regulating the field strength being generated by the external coil(s), or for example to shut off the external coil(s) to stop the recharging process.

A clinician or other user may retrieve data from IMD 15 using external device 11 or another local or networked computing device configured to communicate with processing circuitry 120 via communication circuitry 125, for example through a transceiver such as transceiver 16. The clinician may also program parameters of IMD 15 using external device 11 or another local or networked computing devices. In some examples, the clinician may select patient parameters used to determine times of day and target activity levels to determine when to trigger taking measurements using sensors 127, accelerometers 128, and or via sensing circuitry 122.

In various examples, processing circuitry 120 is configured to receive signals from sensing circuitry 122, sensors 127 including accelerometers 128, and/or sensor signals provided by sensors external to IMD 15, to process these sensor signals to generate one or more input parameters based either directly on or derived from the sensor signals. The input parameters are associated with the value(s) for one or more physiological parameters associated with a patient, such as patient 12 where the IMD 15 may be implanted. The physiological parameters associated with the input parameters may include activity counts, respiration rates, breathing rates, movements, postures, and changes in postures associated with a patient. The values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period.

Similarly, the values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time. These parameters may be used to monitor the physical condition of a patient, and/or to determine the efficacy of a therapy being applied to the patient, and/or the need to apply a new or different therapy, such as a new or different electrical stimulation therapy, to the patient based on analysis if the sensed parameters and/or instructions received by IMD 15 from one or more external devices.

Figure 7:
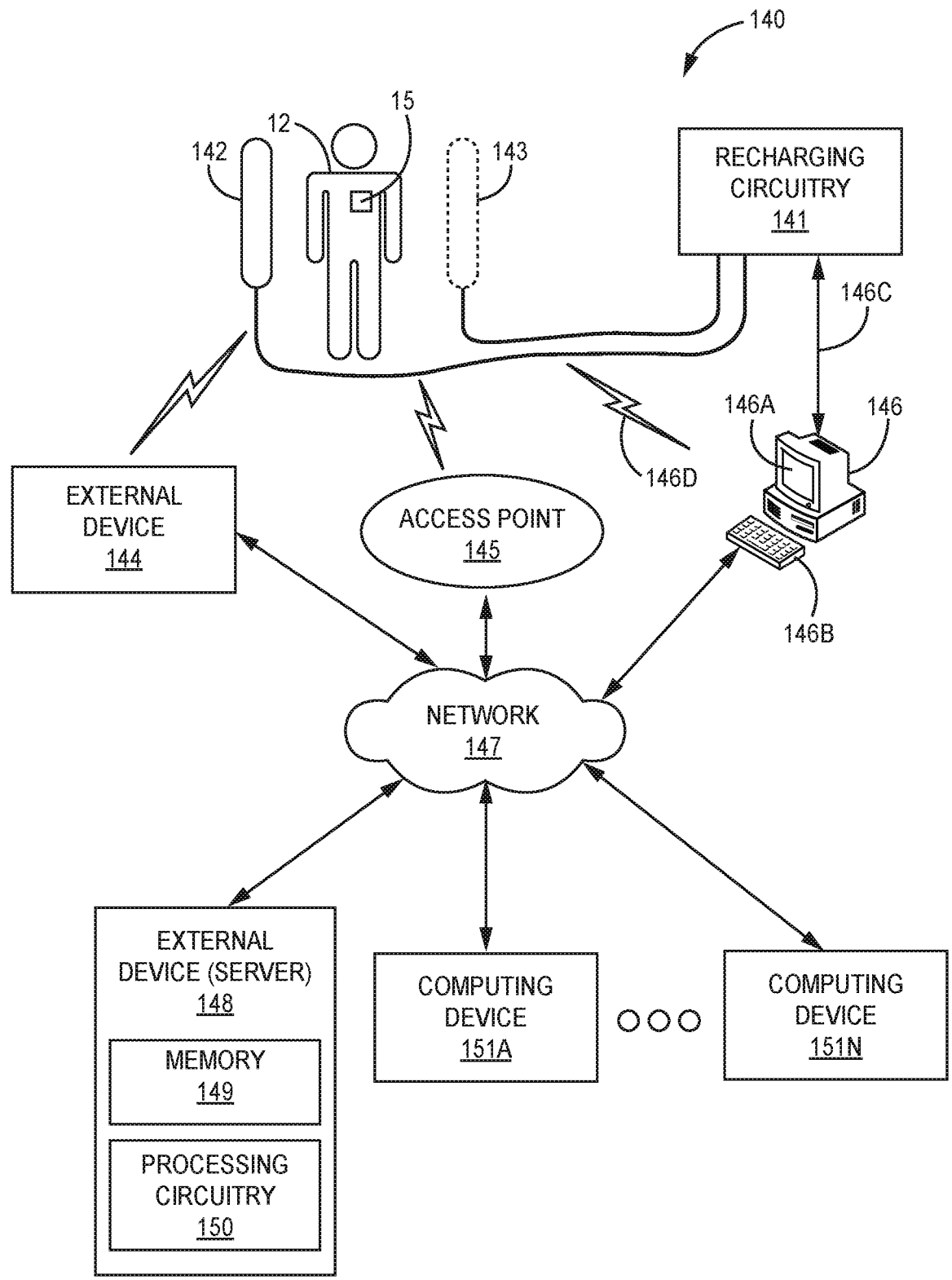
FIG. 7 is a functional block diagram illustrating an example configuration of a system for inductive recharging of an implantable medical device according to various examples described in this disclosure.

FIG. 7 is a functional block diagram illustrating an example configuration of a system 140 for inductive recharging of an implantable medical device 15 according to various examples described in this disclosure. System 140 includes recharging circuitry 141 electrically coupled to a single recharging coil 142 in some examples, or a pair of recharging coils comprising first coil 142 and second coil 143 in some examples, the recharging coil or coils located externally to a patient 12 having an implanted IMD 15 according to the various examples described in this disclosure. In some examples, a single coil 142 may be a flat planar coil arranged to be placed proximate to, and in some examples in direct contact with patient 12 in an area adjacent to IMD 15. Single coil 142 may be electrically energized and configured to provide a time-varying magnetic field that may be imposed on an implanted medical device, such as IMD 15 illustratively represented as being implanted in patient 12, for the purpose of recharging a power source within the 1 MB. In some examples, coil 142 may be arranged as a first coil of a pair of coils including a second coil 143, the pair of coils 142, 143 physically arranged so that when the coils are electrically energized, a time-varying magnetic field is generated between the coils that may be imposed on an implanted medical device, such as IMD 15, for the purpose of recharging a power source within the 1 MB. In some examples, coils 142 and 143 may be physically arranged and electrically configured as a Helmholtz coil. The arrangement of coil 142 and/or coils 142 and 143 relative to patient 12 and IMD 15 as shown in FIG. 7 is not necessarily intended to be illustrative of the actual arrangement, for example with respect to positioning and/or scale of the coil 142 or the pair of coils 142 and 143, and patient 12/IMD 15 during a period of time when recharging of IMD 15 is occurring, and is intended to be illustrative of various features of example system 140.

As shown in FIG. 7, coil 142 (and coil 143 when provided), are coupled to recharging circuitry 141. Recharging circuitry 141 includes various electrical devices arranged to provide and to control the electrical energization of coil 142, and/or coil pair 142/143, in order to generate a magnetic field that may be imposed onto IMD 15 when IMD is positioned proximate to coil 142 or between coil pair 142/143. In various examples, IMD 15 includes a receive antenna located within or coupled to the 1 MB, the receive antenna arranged as an example of any of the multi-axis antennas described in this disclosure, or any equivalents thereof. The multi-axis antenna may be arranged to generate at least a minimum level of induced current in one or more of the coils of the antenna regardless of the direction of orientation of the magnetic field generated by coil 142 and/or coils 142/143 imposed on IMD 15 and for a given PDL applied to the IMD by the imposed magnetic field. As such, an elaborate system of alignment equipment and/or additional and more complex coil alignment procedures may not be required in order to achieve an acceptable level of inductive coupling efficiency between the magnetic field imposed on IMD 15 and the receive antenna of the IMD regardless of the orientation of IMD 15 relative to the direction of the imposed magnetic field.

For example, when recharging a power supply located within IMD 15 while IMD 15 is implanted within patient 12, a single coil 142 may be placed in a position proximate to IMD 15 and external to patient 12, for example covering and/or in contact with an area of patient 12, such as the chest of the patient, adjacent to where 1 MB 15 has been implanted. IMD 15 in some examples may be considered to be a deeply implanted device, for example a device implanted within a chamber of the heart of patient 12. When positioned as described above, coil 142 may be energized to generate a time-varying magnetic field that extends away from coil 142 and is imposed onto IMD 15 and the multi-axis antenna located within IMD 15. Because the receive antenna of IMD 15 is a multi-axis antenna, a precise alignment of the direction of the imposed magnetic field relative to an orientation of IMD 15 and the receive antenna is not critical or required, and may be a random relative orientation. Despite this random relative orientation, at least a minimum level of recharging current may be induced into the receive antenna of IMD 15 for a given level of PDL being provided by coil 142. The lack of a requirement for a precise or a particular alignment between the magnetic field and the orientation of the IMD 15 may allow for efficient and rapid recharging of the power source of the 1 MB without the need for a complex alignment procedure to be performed, and/or without the need for complex alignment apparatus to be provided and operated to align coil 142 and IMD 15. In some examples, simply positioning coil 142 as a single coil proximate to the area of IMD 15, for example laying across an area of the chest of the patient 12 in the area of implantation of IMD 15, is adequate to allow an efficient level of inductive coupling between the magnetic field generated by coil 142 and the multi-axis antenna of the IMD.

In a similar manner, when using a pair of coils 142 and 143 for recharging a power source of IMD 15, the relative alignment of a direction of a magnetic field generated in the area between the coils 142, 143 and the orientation of IMD 15 may not be critical with respect to achieving an efficient level of inductive coupling between the magnetic field and the receive antenna of the IMD. When IMD 15 is positioned in the area between coil pair 142, 143, the coil pair may be energized to generate a time-varying magnetic field extending between the pair of coils, and that may be imposed onto IMD 15 and the multi-axis antenna located within IMD 15. Use of the coil pair 142, 143 may provide a more uniform magnetic field throughout the area between the coils, and thus further reducing or eliminating the need to determine a particular positioning of IMD 15 relative to the position of coils 142, 143 while still providing an efficient level of inductive coupling for inducing a recharging current into the receive antenna of the IMD. Further, because the receive antenna is this example is a multi-axis antenna, an alignment of the direction of the imposed magnetic field generated between coil 142, 143 relative to an orientation of IMD 15 and the receive antenna may not be critical, and may be a random relative orientation. Despite this random relative orientation, at least a minimum level of recharging current may be induced into the receive antenna of IMD 15 for a given level of PDL being provided by the pair of coils 142 and 143.

The lack of a requirement for a precise or a particular alignment between the magnetic field generated by coil pair 142, 143 and the orientation of the IMD 15 may allow for efficient and rapid recharging of the power source of the IMD without the need for a complex alignment procedure to be performed, and/or without the need for complex alignment apparatus to be provided and operated to align coil pair 142, 143 and IMD 15. In some examples, simply positioning IMD 15 within the area between coils 142, 143, for example by positioning coils 142 and 143 on opposite sides of patient 12 so that the longitudinal axis common to both coils aligns with IMD 15, is adequate to allow an efficient level of inductive coupling between the magnetic field generated by the pair of coils 142, 143. and the multi-axis antenna of the IMD. The use of the pair of coils 142, 143 may further simply the requirement for positioning of IMD 15 relative to the coil pair, and the relative level of uniformity of the magnetic field provided between coils 142 and 143 may allow for simply positioning the IMD somewhere in the area between the coils, and energizing the coil pair to achieve an efficient level of inductive coupling between the magnetic field and the receive antenna of the IMD.

Recharging circuitry 141 may be coupled to a computing device 146 that includes a display 146A and one or more input devices 146B, such as a keyboard and/or a computer mouse, that allow a user to interact with recharging circuitry 141 through computing device 146. Computing device 146 may be communicatively linked to recharging circuitry 141 by a wired connection 146C, and/or by a wireless connection 146D. In various examples, computing device 146 is configured to allow a user, such as a physician or a technician (neither shown in FIG. 7), to operate and control recharging circuitry 141 during a recharging session performed on IMD 15. Further, feedback received from IMD 15, for example received by computing device 146, may be used to control and adjust various aspects of recharging circuitry 141, including adjusting the field strength of the magnetic field being imposed on IMD 15, and controlling the duration of the recharging process.

Feedback from IMD 15 in some examples comprises a value for the level of current that is being induced in the receive coil of IMD 15 through the inductive coupling of the energy being provided by coil 142, or by coil pair 142 and 143. Other information provided by IMD 15, such as temperature, rate of charge, and percentage of charge information generated by IMD 15 may be transmitted from IMD 15 to computing device 146 or other external devices, and use by recharging circuitry 141 to control the energization of coils 142 and 143, and/or to determine when to terminate and/or regulate the power level being applied to the recharging process being performed by recharging circuitry 141 on IMD 15.

System 140 further includes external computing devices, such as a server 148 and one or more other computing devices 151A-151N, that may be communicatively coupled to IMD 15, computing device 146, and/or external device 144 via a network 147. In this example, IMD 15 may use its communication circuitry, at different times and/or in different locations or settings, to communicate with external device 144 via a first wireless connection, and/or to communicate with an access point 145 via a second wireless connection. In the example of FIG. 7, computing device 146, access point 145, external device 144, server 148, and computing devices 151A-151N are interconnected, and able to communicate with each other, through network 147.

Access point 145 may comprise a device that connects to network 147 via any of a variety of connections, such as telephone dial-up, digital subscriber line (DSL), or cable modem connections. In other examples, access point 145 may be coupled to network 147 through different forms of connections, including wired or wireless connections. In some examples, access point 145 may be co-located with the patient. Access point 145 may interrogate IMD 15, e.g., periodically or in response to a command from the patient or from network 147, to retrieve physiological measurements and/or other operational or patient data from IMD 15. Access point 145 may provide the retrieved data to server 148 via network 147. In various examples, access point 145 may be any examples of transceiver 16 described above.

In some cases, server 148 may be configured to provide a secure storage site for data that has been collected from IMD 15, from recharging circuitry 141, and/or from external device 144. In some cases, server 148 may assemble data in web pages or other documents for viewing by trained professionals, such as clinicians, via computing devices 151A-151N. The illustrated system 140 of FIG. 7 may be implemented, in some aspects, with general network technology and functionality similar to that provided by the Medtronic® CareLink® Network developed by Medtronic plc, of Dublin, Ireland.

In some examples, one or more of computing device 146, access point 145, server 148, or computing devices 151A-151N may be configured to perform, e.g., may include processing circuitry configured to perform, some or all of the techniques described herein, e.g., with respect to processing circuitry of IMD 15 and external device 144, relating to the recharging of power source located within IMD 15. In the example of system 140 as shown in FIG. 7, server 148 includes a memory 149, which may be configured to store physiological and other data received from IMD 15 and/or external device 144, and processing circuitry 150, which may be configured to provide some or all of the functionality ascribed to processing circuitry of IMD 15 as described herein. For example, processing circuitry 150 may provide programming and/or parameters that are used by recharging circuitry 141 that may be used in the process of providing inductive recharging to a power source located within IMD 15. Configurations for and operational features of coil 142, coil pair 142 and 143, and recharging circuitry 141 may be further described with respect to FIGS. 8-11 of this disclosure.

Figure 8:
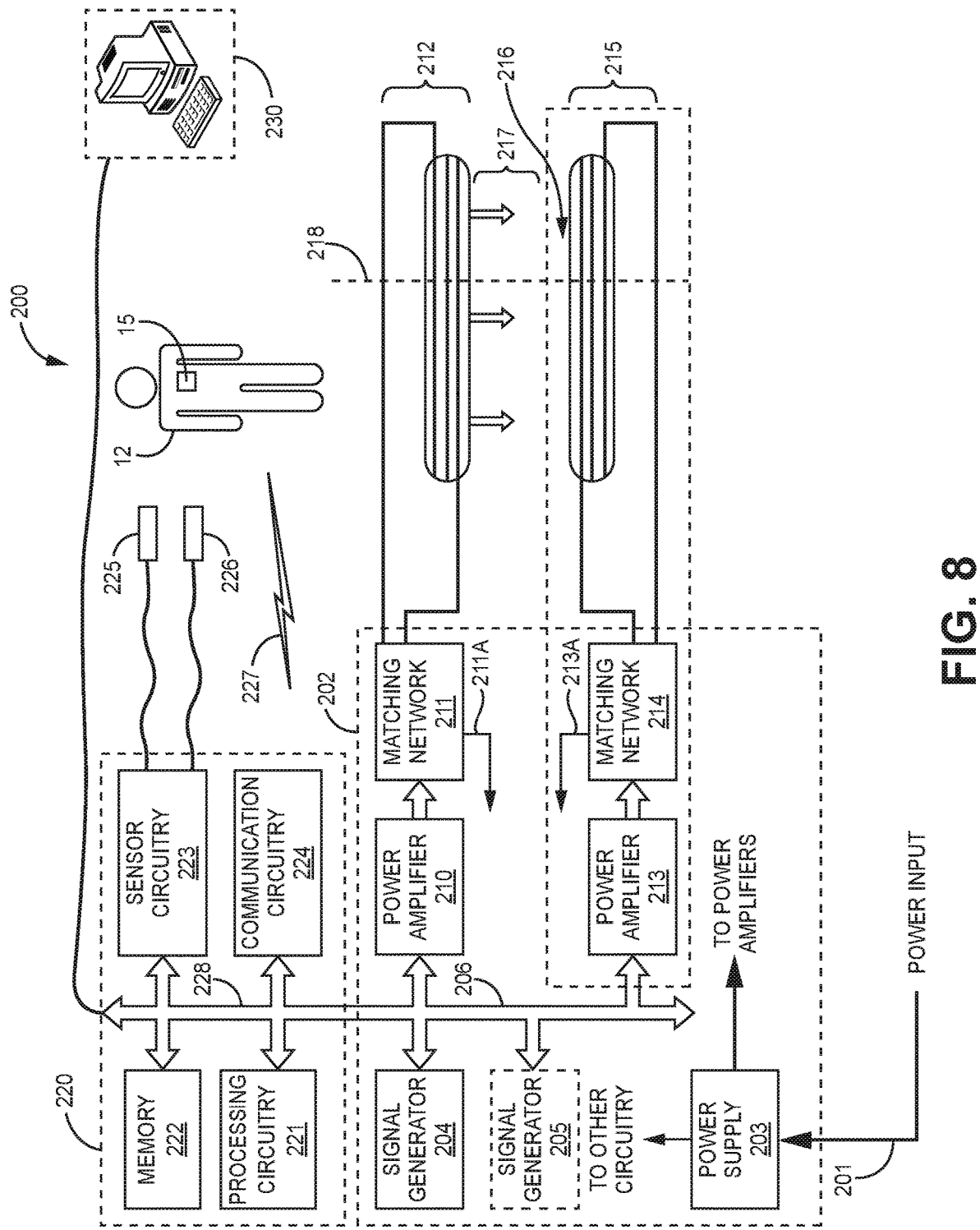
FIG. 8 is a functional block diagram illustrating an example inductive recharging system according to various examples described in this disclosure.

FIG. 8 is a conceptual block diagram illustrating an example recharging system 200 for recharging one or more implantable medical devices implanted in a patient 12 according to various examples described in this disclosure. As illustrated, system 200 may be configured to provide inductive recharging of one or more implanted medical devices, illustratively represented as IMD 15, that are implanted in a patient, illustratively represented as patient 12. System 200 includes recharging circuitry 202 that is coupled to a single coil 212, or a pair of coils 212, 215. The arrangement of coil 212 or the pair of coils 212 and 215 relative to patient 12 and IMD 15 as shown in FIG. 8 is not necessarily intended to be illustrative of the actual physical arrangement, for example with respect to positioning and/or scale of the coil or the pair of coils and patient 12 and IMD 15 during a period of time when recharging of IMD 15 is occurring, and is intended to be illustrative of various features of system 200. The actual arrangements of coil 212, or the actual arrangement of coils 212 and 215 relative to each other, and relative to patient 12 and IMD 15 may be as illustrated and described with respect to coils 142 and coil pair 142/143 as illustrated and described with respect to FIG. 7, and/or as further described below with respect to coils 212 and 215 as illustrated in FIG. 8.

As illustrated in FIG. 8, system 200 includes control circuitry 220 coupled to recharging circuitry 202, and includes processing circuitry 221, a memory 222 coupled to processing circuitry 221, for example by bus/connections 228 (herein after "bus 228"). Memory 222 may store program instructions that, when retrieve and executed by processing circuitry 221, provides programming steps that allow processing circuitry 221 to control recharging circuitry 202 to perform the recharging processes associated with inductively recharging a power source or power sources located within an IMD 15 implanted in patient 12. In addition, memory 222 may also store values, for example charging values, charging times, patient history associated specifically with patient 12, communication protocols, and any other information that may be required or that may be helpful to allow processing circuitry 221 to control the inductive recharging process being used to recharge the power source or sources included in IMD 15 when implanted within patient 12 according to any of the techniques described in this disclosure, and any equivalents thereof.

Control circuitry 220 may include communication circuitry 224. Communication circuitry 224 may be used to receive and process signals from the IMD 15 implanted in patient 12 for use by processing circuitry 221 in controlling the inductive recharging processes including, but not limited to a battery management system that monitors and optimizes the recharge process. Communication circuitry 224 may also provide wireless communications with devices located externally to system 200, for example external device 144, or for example external computing devices 151A-151N, and/or external server 148 as described and illustrated with respect to FIG. 7. In FIG. 8, communication circuitry 224 as may also be used to download information, such as programming information, to control circuitry 220 that may then be stored in memory 222, and accessed by processing circuitry 221.

As described above, memory 222 may be used to store information related to the recharging process performed by system 200, such as the levels of energy provided during a recharging process to coils 212 and/or coil pair 212 and 215, any fault conditions that have occurred during the recharging process, and any other information deemed necessary or helpful that may be related to the recharging processes performed by system 200. This information as stored in memory 222 may be provided to computing device 230, and/or uploaded and transmitted through communication circuitry 224 to some other external device or devices, as described above. Control circuitry 220 as illustrated in FIG. 8 may also include sensor circuitry 223 configured to be coupled one more different sensors 225, 226, and to receive signals from the sensors that may be further processed by sensor circuitry 223 and/or by processing circuitry 221, to provide and/or derive information that may be further used to control and regulate the inductive recharging processes being performed by system 200.

In various examples, one or more of the circuits illustrated as comprising control circuitry 220 may instead be provided by computing device 230. In various examples, computing device 230 includes a display and one or more input devices, such as a keyboard and/or a computer mouse, that allow a user, such as a physician or a clinician, to interact with the system 200. This interaction may include interaction to control the recharging processes to be performed or being performed by system 200. In some examples, computing device 230 is computing device 146 as illustrated and described with respect to FIG. 7, and is configured to provide some combination of or all of the features provided by computing device 146, and to perform some combination or all of the functions ascribed to computing device 146. In some examples, control circuitry 220 and recharging circuitry 202 comprise some or all of recharging circuitry 141 as illustrated and described with respect to FIG. 7, and may provide any of the features and be configured to perform any of the function ascribed to recharging circuitry 141.

As shown in FIG. 8, recharging circuitry 202 includes a power supply 203, a signal generator 204 (which may be comprised of an oscillator and signal generation circuitry), one or more power amplifiers 210 and 213, and one or a plurality of corresponding matching network circuitry 211, 214. The circuits of recharging circuitry 202 may be coupled by a bus/connection 206. Bus 206 may be a same bus as bus 228, or communicatively coupled to bus 228. Recharging circuitry 202 includes a first power amplifier 210 coupled to signal generator 204 and configured to receive a signal from the signal generator 204. First power amplifier 210 is also coupled to matching network circuitry 211, and configured to provide an output signal to the matching network circuitry 211 based on the signal received from the signal generator 204. Matching network circuitry 211 may be configured to provide impedance matching between power amplifier 210 and coil 212, and to provide outputs that may be coupled to coil 212 to energize coil 212.

Recharging circuitry 202 in some examples includes a second power amplifier 213 coupled to signal generator 204, and configured to receive a signal provided by signal generator 204. Second power amplifier 213 is also coupled to matching network circuitry 214, and configured to provide an output signal to the matching network circuitry 214 based on the signal received from the signal generator 204. Matching network circuitry 214 is configured to provide impedance matching between power amplifier 213 and coil 215, and to provide outputs that may be coupled to coil 215 to energize coil 215. In an alternative example, recharging circuitry 202 may include a second signal generator 205 that is coupled to the second power amplifier 213, wherein the second signal generator 205 provides the input signal that is amplified by power amplifier 213 and provided through matching network circuitry 214 to energize coil 215. When the second signal generator 205 is utilized as part of system 200, the second signal generator 205 may be configured to generate an output signal that is phase locked to the output signal generated by the first signal generator 204 so that the output signals provided by the first signal generator 204 and the second signal generator 205 are a same frequency signal and are in-phase with one another.

When system 200 is operating as a single coil recharging system, power amplifier 210 may receive a signal including a waveform generated by signal generator 204, and provide power amplification of the received signal that is then applied through matching network circuitry 211 to energize coil 212. In examples where system 200 is being operated using a coil pair as the recharging coils, power amplifiers 210 and 213 may receive a signal including a waveform generated by signal generator 204, and provide power amplification of the received signal that is then applied through matching network circuitry 211, 214, respectively, to energize coils 212 and 215. Matching network circuitry 211 and 214 provides impedance matching between the output stage of the respective power amplifier that the matching network circuitry is coupled to and the coil that is being energized by that particular power amplifier. In various examples, a typical range of impedance provided as an output from one or more of power amplifiers 210, 213 may be in a range of 1 to 100 ohms, in some examples 50 ohms, wherein the real part of the input impedance of the coils 212, 215 would be in a range of 0.1 to 20 ohms, in some examples 0.5 ohms. The imaginary part of a complex impedance of the coils may be in a range of 60 to several hundred ohms, depending on the frequency of the signal or signal applied to the coils. In order to provide maximum power transfer between the power amplifier outputs and the respective coils these outputs are coupled to, the matching network circuitry 211, 214 are configured to match the impedance of the output of the power amplifier to the coils each power amplifier is coupled to through the respective matching network circuitry.

In some examples, matching network circuitry 211, 214 comprise an impedance matching transformer configured to match an output impedance of a power amplifier to an input impedance of a coil coupled to the output of the impedance matching circuitry. In some examples, matching network circuitry 211, and 214 comprises a transformer and/or a capacitor rated for peak voltage of the assembly and of a capacitance value that the inductive nature of the coil is accommodated. In one implementation, an adjustable vacuum ceramic capacitor is placed in series with a 50Ω to 1Ω transformer. Other configurations and devices may be used to perform the impedance matching function of matching network circuitry 211 and 214, and are contemplated for using in providing the matching network circuitry 211 and 214 as described in this disclosure.

In various examples of system 200, since it is more difficult to dynamically tune the quality factor of the receive antenna within an implanted medical device such as IMD 15, or rather, change the frequency at which the quality factor is a maximum, it may significantly improve the maximum power delivered to IMD 15 by fixing the frequency of the system based on the characteristics of the receive coils and using a tunable vacuum capacitor located between the power amplifier (and after a following transformer) and a coil 212 or a coil pair, such as coils 212 and 215. This technique may be used in order to match the output of the power amplifiers to the impedance presented by the coils without changing the oscillation frequency, as is practiced in other rechargeable wireless power transfer systems such as the RestoreUltra® device from Medtronic plc, of Dublin, Ireland. A frequency based maximization configuration may result in a non-optimal power transfer if the secondary/receive coils of IMD 15 are tuned to a frequency different than that found to maximize power transfer to the primary/transmit coils providing the inductive energy provide by system 200. Therefore, examples of the systems and methods described herein comprise tuning the impedance of the system at a fixed frequency, as opposed to varying the frequency of the system, in order to maximize the power delivered to a receive coil in the implanted device being recharged by the system.

As shown in FIG. 8, power supply 203 is coupled to a power input 201, and is configured to receive electrical power from power input 201. Power input 201 may be any source of electrical power, such as commercially available electrical power supplied by an electrical utility, for example electrical power having 110-120 volts RMS single-phase power at a frequency of 50-60 Hz, as that is commonly available in the United States. In other examples, power input 201 may provide power in other arrangements, such as but not limited to 480 volt three-phase power in an ungrounded delta configuration at 50-60 Hz, or 208 three-phase "Y" center grounded configuration at 50-60 Hz. Other voltages, frequencies, configurations, and numbers of phases are contemplated for use as the power input 201 to system 200, as would be understood by one of ordinary skill in the art. Power supply 203 is configured to receive electrical power from power input 201, and may perform various operations on the received electrical power, including conditioning, filtering, and conversion of the input power voltage to one or more different voltages, including both different voltages provided as alternating current (AC) voltage supplies and direct current (DC) power supplies as outputs from power supply 203. These power outputs are generally represented by the "TO OTHER CIRCUITRY" output arrow illustratively provided as an output from power supply 203, and may include any electrical power outputs required to power the circuitry for operation of the devices included in and powered from system 200.

In some examples, power supply 203 is also configured to provide one or more separate outputs, illustratively represented by the "TO POWER AMPLIFIERS" output arrow from power supply 203. These outputs from power supply 203 may be directly coupled to power amplifiers 210 and 213 provided as part of recharging circuitry 202, and wherein the "TO POWER AMPLIFIERS" output is configured to provide the electrical energy used to energize the coil 212 and/or coil pair 212, 215 under the control of the power amplifiers 210 and 213, respectively.

In FIG. 8, signal generator 204 is coupled to bus 206, wherein signal generator 204 may be configured to generate one or more output signals that are used to control the waveforms of the electrical power used to energize coil 212 and/or coil pair 212, 215. For example, signal generator 204 may generate a signal having sinusoidal voltage waveform and a particular frequency. This signal is provided to the power amplifier(s) and matching network circuitry of recharging circuitry 202. In some examples, the sinusoidal waveform is converted to a square waveform, the frequency of the square waveform having a same frequency of the sinusoidal waveform generated by signal generator 204, or in other examples signal generator 204 may change the frequency of the square waveform signal. In some examples, the duty cycle of the square wave may be the same as provided with the sinusoidal waveform (e.g., a 50% duty cycle), and in other examples, signal generator 204 may alter the duty cycle to a duty cycle other than a 50% duty cycle for the square waveform signal.

In some examples, signal generator 204 amplifies the signal for example to alter the voltage level of the signal. In some examples, signal generator 204 is configured to process the signal to retain the processed signal as a sinusoidal waveform, but for example acts as a buffer or driver to amplify and/or drive the output signal from the signal generator 204 to the power amplifier 210 and/or amplifiers 210 and 213, and for example to prevent the power amplifiers from loading down or otherwise distorting the signal being provided from the signal generator 204. In some examples, one or more of the power amplifiers comprise a Class D amplifier. In some examples, one or more of the power amplifiers comprise a Class E amplifier. In some examples, the signal generator 204 may provide recharge frequency tuning (closed loop or open loop), to optimize the wireless power transfer between coil 212 or coil pair 212, 215 and the receive antenna of IMD 15. This tuning may or may not be integrated and coordinated with the battery management system and telemetry/communication systems.

Once processed by signal generator 204, the signal generator 204 is coupled to power amplifier 210 that is configured to control the output of electrical energy provided by matching network circuitry 211 to coil 212 using the signal processed by signal generator 204, which may be provided by a coupling the power amplifier 210 to the "TO POWER AMPLIFIER" output of power supply 203. The output from power amplifier 210 is then provided as an output to matching network circuitry 211 to energize coil 212. Matching network circuitry 211 may also include a feedback 211A loop that provides a feedback signal, such as a varying voltage level, that is indicative of the level of energy, for example a current flow, being provided to coil 212 by matching network circuitry 211. This feedback signal may be processed by one or more devices included in system 200, for example processing circuitry 221 or computing device 230, or other battery management systems, to provide information that may be used to control and regulate the output of electrical energy being provided to energize coil 212. Energization of coil 212 may provide a magnetic field, generally indicated by arrows 217, that extend away from coil 212, for example in a direction defining a direction for the magnetic field.

When operating system 200 as a single recharging coil system, electrical energy may be provided to only coil 212, and coil 215 may not be provided as part of system 200. When energizing coil 212 as a single recharging coil system, coil 212 may be a flat planar coil having a spiral wound coil configuration. In some examples, the flat planar coil may include an electrical conductor, such as 4500/48 Litz wire, forming 20 turns extending in a flat spiral shaped arrangement and having a diameter of approximately 50 centimeters. In some examples, the flat planar coil may include an electrical conductor, such as 105/40 Litz wire, forming 12 turns of the conductor extending in a flat spiral shaped arrangement and having a diameter of approximately 30 centimeters. Other variations in the types of wire, the number of turns, and/or the diameter of the coils may be used, and are contemplated for use in the single coils systems of system 200. For example, 4500/48 Litz wire may also be used to form the 30-centimeter diameter coil.

In examples using a single planar recharging coil for coil 212, the direction (e.g., the angle) of magnetic field 217 relative to coil 212 may vary based on the distance and position from the coil. For example, portions of the magnetic field closest to coil 212 may have a magnetic field direction that is generally perpendicular to the coil, and parallel to longitudinal axis 218 of the coil. As the distance from coil 212 increases, the direction of magnetic field may change, and vary through a range of angles relative to the surface of the coil 212 and relative to longitudinal axis 218 so that at some distance from the coil the direction of the magnetic field is parallel to the surface of the coil 212 and is perpendicular to the longitudinal axis 218. When an IMD such as IMD 15 is placed adjacent to coil 212, for example by placing coil 212 on an exterior surface of patient 12 in the area where IMD 15 is implanted, the direction of the portion of the magnetic field that is imposed on the IMD, and thus on the receive antenna within the IMD, is variable based for example on the depth of the implanted device within the patient and thus the distance of the receive antenna from the surface of the coil 212. As described above, the multi-axis antenna of IMD 15 is configured to provide at least a minimum level of induced recharging current for a given power level of the imposed magnetic field regardless of the orientation of the direction of the magnetic field relative to the orientation of the receive antenna. As such, an effective level of inductive coupling may be achieved between the magnetic field generated by coil 212 and the receive antenna of IMD 15 during a recharging session by simply placing coil 212 on or near the external surface of patient 12 in the area of implantation of IMD 15 without the need for complex alignment procedures to be performed and without the need for complex apparatus to align the position and/or angular orientation of coil 212 relative to patient 12 and IMD 15.

When operating system 200 using the coil pair 212, 215, signal generator may provide a signal to power amplifier 210 to energize coil 212 through matching network circuitry 211 as described above. In addition, signal generator 204 may also provide a signal to power amplifier 213, which receives power from the "TO POWER AMPLIFIERS" output from power supply 203, and provides an output to matching network circuitry 214 to electrically energize coil 215. Power amplifier 213 and matching network circuitry 214 may be configured to operate and to provide any of the features and functions described above with respect to power amplifier 210 and matching network circuitry 211, respectively, in providing the electrical energy used to energize coil 215. In addition, matching network circuitry 214 includes a feedback signal 213A, that may be used in same or similar matter as described above with respect to feedback signal 211A, but for use in controlling and regulation of power amplifier 213 and the matching network circuitry 214 with respect to providing the electrical energy used to energize coils 215.

In various examples, the same signal is provided by signal generator 204 to both power amplifier 210 and to power amplifier 213. The power amplifiers 210, 213 may then process the signal and control matching network circuitry 211 and 214, respectively, so that a same level of electrical energy is provided to both sets of coils 212 and 215 at any given time when coils 212 and 215 are energized. The polarity of the electrical power provided to coils 212 and 215 may be arranged such that the coils generate a generally uniform resultant magnetic field throughout the area 216 between the coils, the resultant magnetic field generally indicated by arrows 217. For example, coils 212 and 215 may be physically constructed and arranged relative to one another to form a Helmholtz coil. A Helmholtz coil in some examples consists of a pair of coils, each coil having a circular-shaped winding encircling a portion of a longitudinal axis such as axis 218 that is common to both coils, each of the coil windings generally formed in a plane or a set of planes that are perpendicular to the longitudinal axis, the coils having windings that are themselves coplanar to each other and separated by a distance along the longitudinal axis that is equal to a value for the radius of each of the circular-shaped coil winding.

In some examples, the resultant magnetic field formed in area 216 between coil pair 212 and 215 may have a magnetic field direction that is generally parallel with longitudinal axis 218 throughout the area 216, and having an orientation that extends from coil 212 toward coil 215 or that extends from coil 215 toward coil 212 depending on the polarity of the electrical energy applied to each coil. Because the magnetic field intensity and the direction of the magnetic field in the area 216 is generally consistent throughout area 216, the precise positioning of patient 12 and IMD 15 between coils 212, 215 is not critical, and positioning patient 12 so the IMD 15 is located within area 216 may be sufficient to impose the magnetic field onto the receive antenna of IMD 15 so that efficient inductive coupling may be achieved between the magnetic field and the receive antenna.

As described above, the multi-axis antenna of IMD 15 is configured to provide at least a minimum level of induced recharging current for a given power level of the imposed magnetic field regardless of the orientation of the direction of the magnetic field relative to the orientation of the receive antenna. As such, an effective level of inductive coupling may be achieved between the uniform magnetic field generated by the coil pair 212, 215 and the receive antenna of IMD 15 during a recharging session by simply placing IMD 15 within area 216 between coils 212 and 215 without the need for complex alignment procedures to be performed, and without the need for complex apparatus to align the position and/or angular orientation of coil pair 212, 215 relative to patient 12 and IMD 15.

In operation, a patient 12 with at least one IMD 15 that requires recharging of the power source located within the at least one IMD 15 is positioned so that the IMD 15 is located within the area of the magnetic field that will be generated by coil 212 when operating system 200 as a single recharging coil configuration, or so that IMD 15 is located within the area between coils 212 and 215 when operating system 200 using a pair of recharging coils. Based on control provided by processing circuitry 221 and/or by instructions received from computing device 230, signal generator 204 generates one or more signals that are provided to the power amplifier 210 and/or amplifiers 210 and 213. The power amplifier(s), based at least in part on the received signal, and in some examples based on instructions received from processing circuitry 221, provide power outputs to energize coil 212 or the pair of coils 212 and 215. When energized, the coil(s) generate a magnetic field (or a resultant magnetic field) that that is imposed onto the receive antenna of IMD(s) 15, which begins to provide inductive charging current to the power source located in IMD 15. Signals either provided by IMD 15 to communication circuitry 224 and/or signals provided as feedback signal(s) 211A, and 213A, are processed, for example by processing circuitry 221, and may be used to regulate the energy levels applied to the coil 212 or the coil pair 212, 215.

During the process of inductively recharging the power source located in IMD 15, various sensors 225, 226, may be monitored, and the information received from or derived from the sensors may be used to further control the recharging process. For example, temperature sensors located at the coils may provide signals indicative of the temperatures of coils 212, 215, and may be monitored during the recharging process to determine if one or more of the coils may be overheating. In some examples, one or more of sensors 225, 226 may sense a magnetic field strength and/or direction of the resultant magnetic field at one or more locations in the area proximate to coil 212 or the area 216 between coils 212 and 215. The information from the one or more sensors 225, 226 may be received at sensor circuitry 223, and may be further processed, for example by processing circuitry 221, and used as a further basis for control of the recharging process being performed by system 200. For example, the level of the intensity of the magnetic field being generated by coil 212 or coil pair 212 and 215 as sensed by the one or more sensor 225, 226 and may be monitored to assure that a safe level of exposure to the electromagnetic fields provided to the patient 12 are maintained.

In some examples, a temperature of the patient 12 and/or of IMD 15 may be monitored during the recharging process. These sensed temperatures of patient 12 and/or of IMD 15 may be used to control the recharging process for example by lowering (reducing) the level of energy being provided to the coils if the temperature of the patient 12 or of IMD 15 is rising, and for example shutting off the energy or lowering the energy level being provided to the coil or pair of coils if the temperature of the patient 12 or of IMD 15 exceeds a temperature considered to be safe for the patient. Further, the strength of the magnetic field being generated and imposed on IMD 15 may be monitored during the recharging process, and the sensed strength of the magnetic fields may be processed and used to further regulate the process, for example to raise or lower the level of electrical energy being provided to the coils. Monitoring of the strength of the magnetic field imposes on the patient 12 may be required to assure that the level of the strength of the magnetic field does not exceed a predetermined level, or a predetermined level for more than a predetermined time period. The monitoring may include a reduction, including lower the energy level or shutting off the electrical energy provided to the coils for safety reasons if the strength of the magnetic field exceeds some predetermined value or values, either instantaneous and/or over some predetermined time period.

In various examples, processing circuitry 221 regulates various functions related to the recharging process. Processing circuitry 221 may include a timer function for controlling and limiting the duration of time the patient 12 may be exposed to the magnetic fields being generated by coil 212 or coil pair 212, 215 during the recharging process. Timing functions may be provided by one or more timers included in processing circuitry 221, and may timeout based on one or more timer values stored in memory 222. Processing circuitry 221 may also regulate a profile of the levels of electrical energy provided to the recharging coil or coil pair over the duration of the recharging process, so that the levels of electrical energy provided to coil 212 or to each of the coils 212 and 215 may be set and/or varied over the duration of the recharging process based on a profile that may be stored in memory 222 and retrieved and executed by processing circuitry 221.

In some examples, IMD 15 may provide a signal (e.g., wireless signal 227) to communication circuitry 224 that indicates the level of recharge that has been provided to the power source within IMD 15. Processing circuitry 221 may further regulate and/or terminate the recharging process of IMD 15 based on this information. For example, a wireless signal 227 provided by IMD 15 may indicate that the power source located within IMD 15 is fully recharged, and further exposure to the magnetic fields by both patient 12 and IMD 15 will provide no further charging of the power source. In such instances, processing circuitry 221 may terminate the recharging process in order to minimize the amount of exposure of patient 12 to the magnetic fields generated by system 200, regardless of whether or not a timer has indicated that the time for recharging the power source of IMD 15 has expired.

Figure 9:
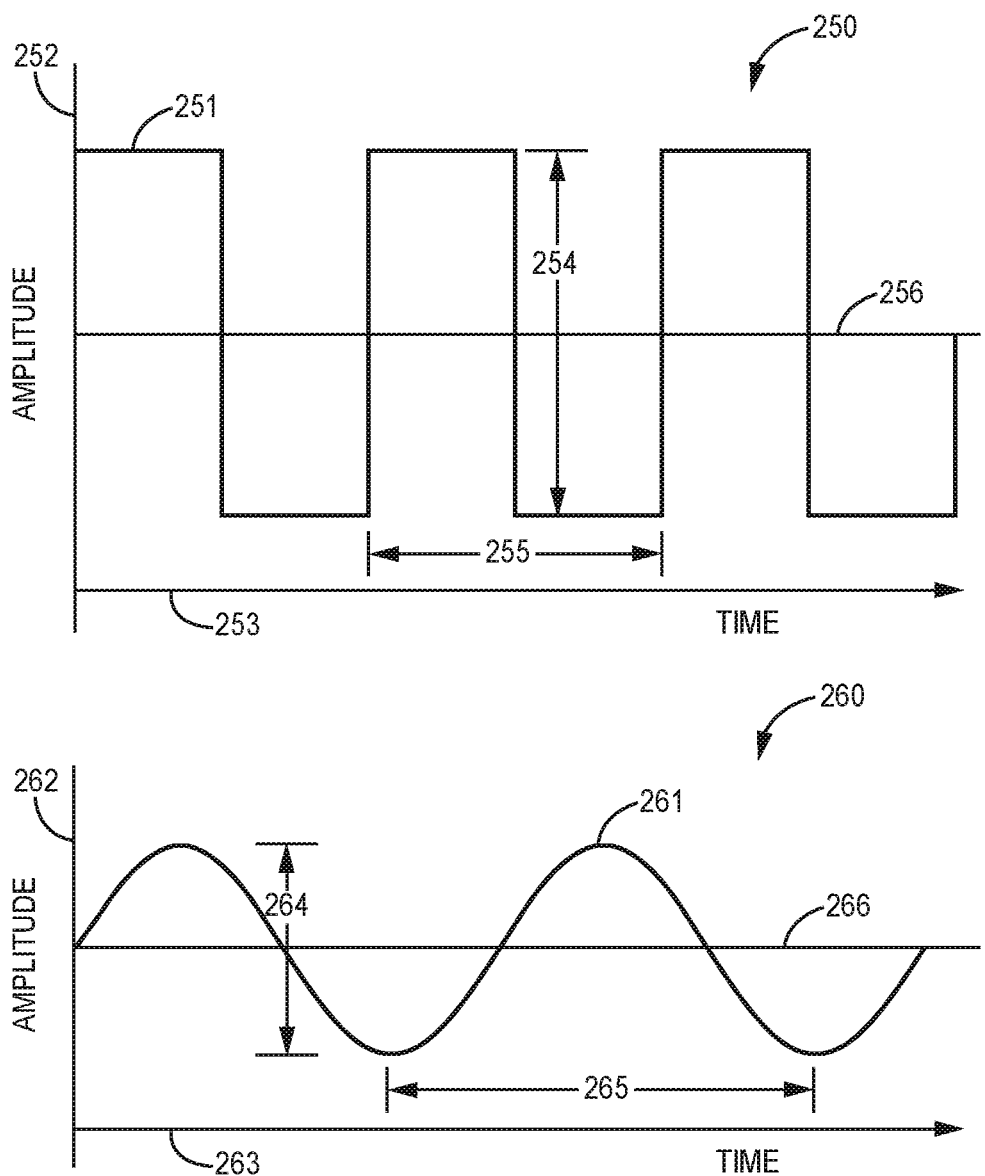
FIG. 9 illustrates graphs of representative waveforms that may be generated by a signal generator and applied to the recharging coil or coils of a recharging system according to various examples described in this disclosure.

FIG. 9 illustrates graphs 250, 260 of representative waveforms 251, 261 that may be generated by a signal generator and applied to the recharging coil or coils of a recharging system according to various examples described in this disclosure. The representative waveforms 251, 261 may be generated by a signal generator, such as signal generator 204 and/or signal generator 205 as illustrated and described with respect to FIG. 8, and applied to the coil (e.g., coil 142 of FIG. 7; coil 212 of FIG. 8), or a pair of coils (e.g., coils 142 and 143 of FIG. 7; coils 212 and 215 of FIG. 8) coupled to recharging circuitry according to various examples described in this disclosure. In FIG. 9, graph 250 illustrates the example waveform 251 of a square wave having an amplitude value plotted against the vertical axis 252 over time, time represented by horizontal axis 253. Waveform 251 comprises a peak-to-peak amplitude 254, and a cycle period 255. In various examples, the peak-to-peak amplitude 254 of waveform 251 may comprise a voltage range of 10 mV to 100 volts, in some examples, 5 volts. The peak-to-peak amplitude in some examples is dependent on the power amplifier selected that the waveform 251 is being provided to in order to generate the output used to energize one coil or a pair of electrical coils arranged as recharging coils in a recharging system.

In some examples, the power amplifier being driven by the waveform 251 is a fixed amplification power amplifier, capable of providing a 400-Watt output signal based on a variable input signal having a peak-to-peak amplitude 10-200 mV. In some examples, a reference voltage level 256 may comprise a zero-volt reference voltage, wherein a portion of waveform 251 is provided at voltage level that is a higher voltage than the reference voltage 256, and a portion of waveform 251 is provided at a voltage level that is less than the reference voltage level 256. In various examples, the duty cycle of waveform 251 over period 255 provides a fifty-percent duty cycle. In various examples, the duty cycle of waveform 251 over the period 255 provides a duty cycle other than a fifty-percent duty cycle. In various examples the time period 255 of waveform 251 is in a range of 100 microseconds to 100 nanoseconds, representative of a frequency range of 10 kHz to 10 MHz for waveform 251.

In some examples, an electrical voltage having a waveform corresponding to waveform 251 may be applied to a single recharging coil to generate a magnetic field that may be imposed on a multi-axis antenna of an implanted medical device to induce a recharging current into the antenna for the purpose of recharging a power source of the implanted medical device. The multi-axis antenna may be any of the examples of the multi-axis antenna described throughout this disclosure configured to provide at least a minimum level of recharging current for a given energy level associated with the imposed magnetic field regardless of the orientation of the direction of the magnetic field generated by the single recharging coil relative to the orientation of the implanted medical device and the multi-axis antenna.

In some examples, an electrical voltage having a waveform corresponding to waveform 251 may be applied to a pair of coils to generate a generally uniform magnetic field between the pair of coils that may be imposed on a multi-axis antenna of an implanted medical device positioned in an area between the pair of coils. The uniform magnetic field may be used to induce a recharging current into the multi-axis antenna for the purpose of recharging a power source of the implanted medical device. The multi-axis antenna may be any of the examples of the multi-axis antenna described throughout this disclosure configured to provide at least a minimum level of recharging current for a given energy level associated with the imposed magnetic field regardless of the orientation of the direction of the uniform magnetic field generated by the pair of coils relative to the orientation of the implanted medical device and the multi-axis antenna.

In some examples, electrical energy having the same electrical parameters such as amplitude, duty cycle, and phase for waveform 251 is applied to each of the pair of coils being utilized as the recharging coils. Other and/or different combinations of differences between the electrical parameters of waveform 251 applied to the first electrical coil and at a same time to the second electrical coil is not limited to variation of the amplitude 254 of the waveforms, and may include other variation, such as differences in the duty cycle of the waveforms applied for example to the first coil compared to a duty cycle of the waveform that is applied to the second electrical coil.

Graph 260 illustrates an example waveform 261 of a sinusoidal waveform having a varying amplitude value plotted against the vertical axis 262 over time, time represented by horizontal axis 263. Waveform 261 comprises a peak-to-peak amplitude 264, and having a period 265. In various examples, the peak-to-peak amplitude 264 of waveform 261 may comprise a voltage range of 10 mV to 100 volts, in some examples, 5 volts. The peak-to-peak amplitude in some examples is dependent on the desired peak magnetic field intensity and the capacity of the power amplifier employed. In some examples, the power amplifier being driven by waveform 261 is a fixed 400-Watt power amplifier, in other example the power amplifier comprises a variable output between 2 Watt and 1 kW. In some examples, a reference voltage level 266 may comprise a zero-volt reference voltage, wherein a portion of waveform 261 provides a voltage level above the reference voltage level 266, and another portion of each cycle of waveform 261 comprises voltage value that is below the reference voltage level 266. In various examples, the duty cycle of waveform 261 over period 265 provides a fifty-percent duty cycle of voltage levels above the reference voltage level 266. In various examples the time period 265 of waveform 261 is in a range of 100 microseconds to 100 nanoseconds, representative of a frequency range of 10 kHz to 10 MHz for waveform 261.

In some examples, an electrical voltage having a waveform corresponding to waveform 261 may be applied to a single recharging coil to generate a magnetic field that may be imposed on a multi-axis antenna of an implanted medical device to induce a recharging current into the antenna for the purpose of recharging a power source of the implanted medical device. The multi-axis antenna may be any of the examples of the multi-axis antenna described throughout this disclosure configured to provide at least a minimum level of recharging current for a given energy level associated with the imposed magnetic field regardless of the orientation of the direction of the magnetic field generated by the single recharging coil relative to the orientation of the implanted medical device and the multi-axis antenna.

In some examples, an electrical voltage having a waveform corresponding to waveform 261 may be applied to a pair of coils to generate a generally uniform magnetic field between the pair of coils that may be imposed on a multi-axis antenna of an implanted medical device positioned in an area between the pair of coils. The uniform magnetic field may be used to induce a recharging current into the multi-axis antenna for the purpose of recharging a power source of the implanted medical device. The multi-axis antenna may be any of the examples of the multi-axis antenna described throughout this disclosure configured to provide at least a minimum level of recharging current for a given energy level associated with the imposed magnetic field regardless of the orientation of the direction of the uniform magnetic field generated by the pair of coils relative to the orientation of the implanted medical device and the multi-axis antenna.

In some examples, electrical energy having the same electrical parameters such as amplitude, duty cycle, and phase for waveform 261 is applied to each of the pair of coils being utilized as the recharging coils. Other and/or different combinations of differences between the electrical parameters of waveform 261 applied to the first electrical coil and at a same time to the second electrical coil is not limited to variation of the amplitude 264 of the waveforms, and may include other variation, such as differences in the phases of the waveforms applied for example to the first coil compared to the second coil.

Figure 10:
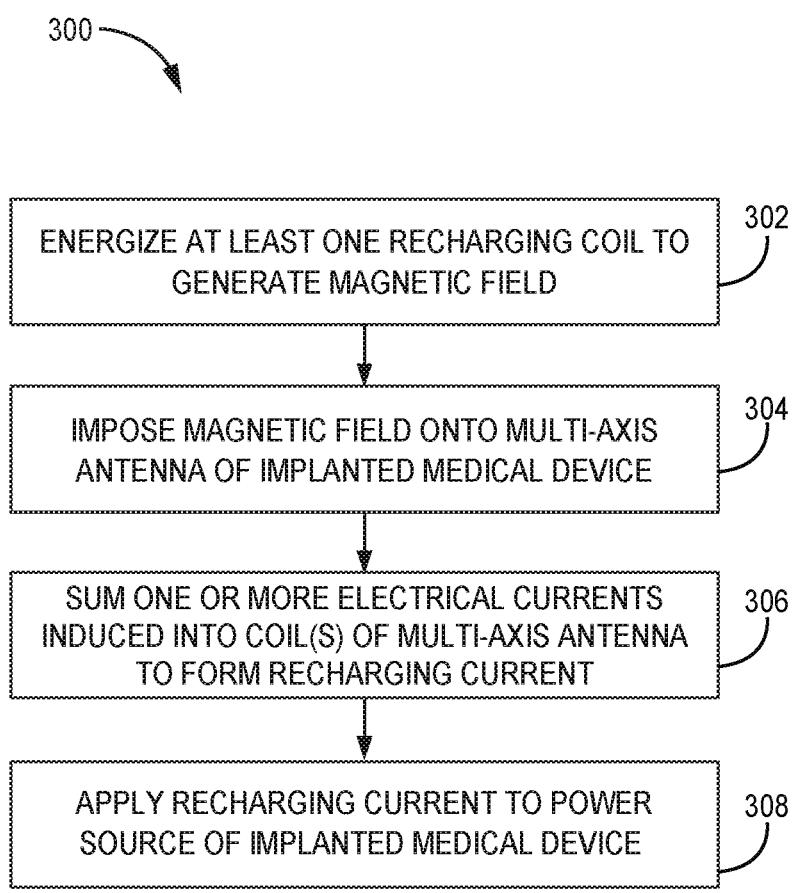
FIG. 10 is a flowchart illustrating a method according to various examples described in this disclosure.

FIG. 10 is a flowchart illustrating a method 300 according to various examples described in this disclosure. Method 300 includes recharging a power source located in an implanted medical device implanted within a patient. Method 300 is described as being performed by system 200 as illustrated and described with respect to FIG. 8, the recharging process performed on implantable medical device 30 having a multi-axis antenna 40 located within the device as illustrated and described with respect to FIG. 2. However, method 300 is not limited to being performed examples of system 200 performing the recharging process on an implanted medical device, and method 300 is not limited to recharging processes performed on examples of device 30. Other devices having examples of the multi-axis receive antennas as described throughout this disclosure, and any equivalents thereof, that are configured to have recharging currents induced into the antenna for the purpose of recharging a power source of the implanted medical device are contemplated by the processes of method 300.

Method 300 includes a recharging circuitry 202 of system 200 energizing at least one recharging coil, e.g., coil 212 or a pair of coils 212, 215, to generate a magnetic field 217 (block 302). In instances where the recharging coil is a single recharging coil, such as coil 212, the recharging coil may be a flat planar coil according to any of the examples described throughout this disclosure. In instances where the recharging coil is a pair of coils, such as coils 212 and 215, the pair of coils may be physically arranged and electrically energized according to any of the pairs of coils described throughout this disclosure, including coils 212 and 215 arranged to form a Helmholtz coil.

Method 300 includes imposing the generated magnetic field onto a multi-axis (receive) antenna 40 of the implanted medical device 30 having a rechargeable power source, such as battery 39, that is to be recharged (block 304). In some examples where a single recharging coil is being utilized to generate the magnetic field, imposing the magnetic field onto the multi-axis antenna may include placing the recharging coil proximate to, and in some examples in contact with, an exterior area or surface of the patient having the implanted medical device to be recharged adjacent to the location of the implanted device. In some examples where a pair of coils is being utilized to generate the magnetic field, imposing the magnetic field onto the multi-axis antenna may include positioning the patient, and thus the implanted medical device 30, within an area located between the pair of coil 212, 215. The multi-axis antenna of the implanted device may include any of the examples of multi-axis antenna, such as antenna 89 as illustrated and described with respect to FIG. 4, which may be positioned within, e.g., encircled by an antenna window 42 of device 30 as illustrated and described with respect to FIG. 2. In various examples, the multi-axis antenna includes a ferrite core that is encircled, at least partially, by each of the coil windings forming the antenna 89.

Method 300 includes summing, by recharging circuitry, one or more electrical currents induced into one or more of the coils of the multi-axis antenna to generate a recharging current (block 306). Summing the induced electrical currents to may include coupling each of the coils of the multi-axis antenna to an individual diode, such as diodes 54, 57, and 60 as illustrated and described with respect to schematic diagram 50 and FIG. 3. In various examples, summing the induced electrical currents may include filtering the current or currents generated in one or more of the coils of the multi-axis antenna using one or more capacitors, such as capacitor 61 as illustrated and described with respect to schematic diagram 50 and FIG. 3.

Referring to FIG. 10, method 300 includes applying, by recharging circuitry, the generated recharging current to the power source, such as battery 39, of the implanted medical device 30 (block 308). In various examples, applying the recharging current to the power source includes controlling the coupling of the recharging current to a power source, such as power source 62, through a switching device, such as switching device 92, the switching device controlled by recharging circuitry, such as recharging circuitry 90 as illustrated and described with respect to schematic diagram 50 and FIG. 3.

Figure 11:
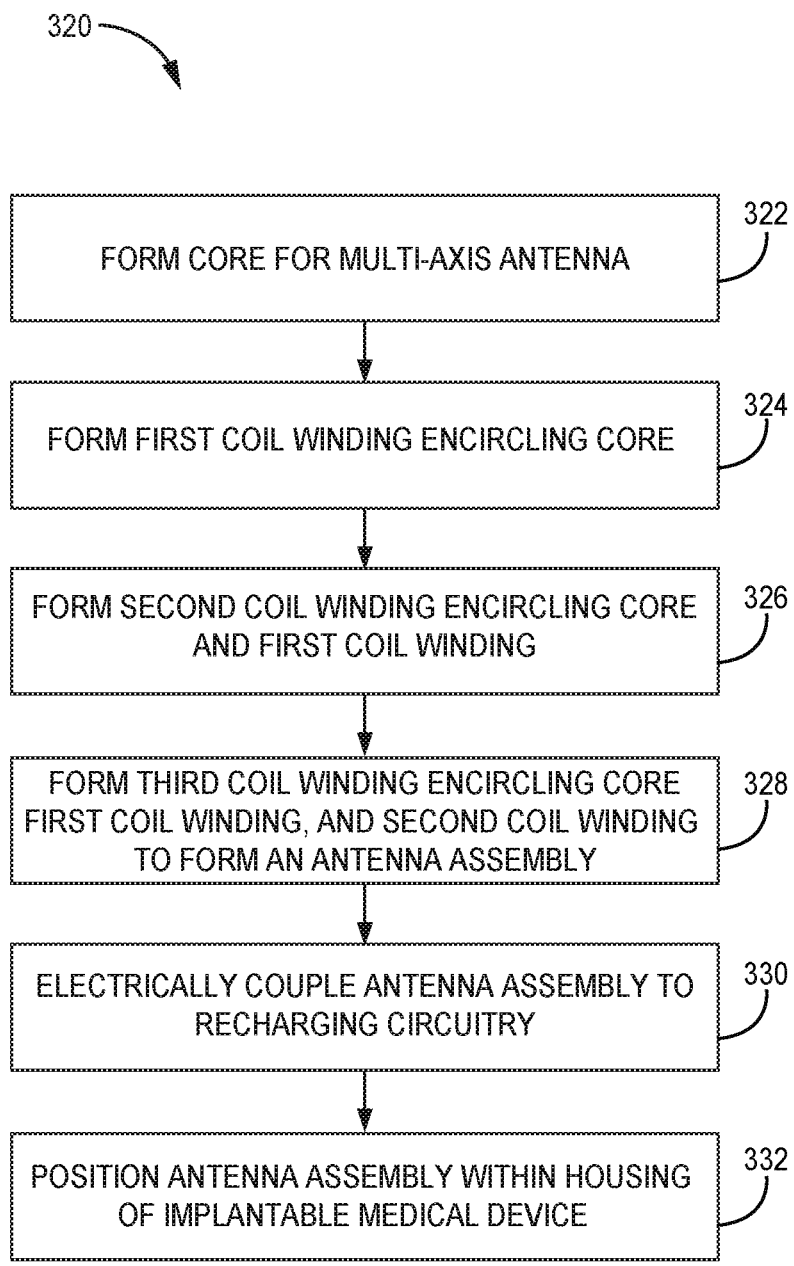
FIG. 11 is a flowchart illustrating a method according to various examples described in this disclosure.

FIG. 11 is a flowchart illustrating a method 320 according to various examples described in this disclosure. Method 320 includes a method for manufacturing a multi-axis antenna for an implanted medical device that is to be implanted within a patient. Method 320 is described as manufacturing an implantable device 30 designed to be implanted within a chamber of the heart of a patient, and to include a multi-axis antenna configured to generate a recharging current when a magnetic field is imposed on the antenna, the recharging current for recharging a power source (e.g., battery 39) of the device 30. However, method 320 is not limited to manufacturing the implantable medical device 30 having the multi-axis antenna as illustrated and described for example with respect to FIG. 2, and may be applied to the manufacture of a variety of implantable medical devices having a multi-axis antenna according to the examples of multi-axis antenna and implantable medical devices as described throughout this disclosure, and any equivalents thereof.

Method 320 includes forming a core 85 for the multi-axis antenna (block 322). Core 85 in some examples is formed from a ferrite material. In some examples, the core 85 is formed to have a cubic shape having a same value for a height, a width, and a depth dimension of the core. Core 85 in some examples has a value for each of the height, width, and depth dimension of three millimeters, having a total volume for the core of twenty-seven cubic millimeters.

Method 320 includes forming a first coil 71 comprising a winding encircling the core (block 324). The first coil winding may be formed of an electrically conductive wire, such as Litz wire. The first coil winding may be formed to include an interior space, the winding formed to encircle the core so that the core is at least partially included within the interior space of the first coil winding. First coil winding may encircle a first coil axis of orientation forming a normal axis for the first coil. The first coil winding may encircle the core so that the first coil winding extends along the outer surfaces of the core along two of the three dimensions of the core.

Method 320 includes forming a second coil 80 comprising a winding encircling the core and encircling the first coil winding (block 326). The second coil winding may be formed of an electrically conductive wire, such as Litz wire. The second coil winding may be formed to include an interior space, the winding formed to encircle the core so that the core is at least partially included within the interior space of the second coil winding. The second coil winding may encircle a second coil axis of orientation forming a normal axis for the second coil, the second coil axis of orientation orthogonal to the first coils axis of orientation. The second coil winding may encircle the core so that the second coil winding extends along the outer surfaces of the core along two of the three dimensions of the core, at least one of the two dimensions that is different from the two dimensions encircled by the first coil winding.

Method 320 includes forming a third coil 76 comprising a winding encircling the core, encircling the first coil winding, and encircling the second coil winding to form an antenna assembly (block 328). The third coil winding may be formed of an electrically conductive wire, such as Litz wire. The third coil winding may be formed to include an interior space, the winding formed to encircle the core so that the core is at least partially included within the interior space of the third coil winding. The third coil winding may encircle a third coil axis of orientation forming a normal axis for the third coil, the third coil axis of orientation orthogonal to both the second coil axis of orientation and the first coils axis of orientation. The third coil winding may encircle the core so that the third coil winding extends along the outer surfaces of the core along two of the three dimensions of the core, at least one of the two dimensions that is different from one of the two dimensions of the core encircled by the first coil winding, and at least one of the two dimensions encircled by the third coil winding different from one of the two dimensions of the core encircled by the second coil winding.

Method 320 includes electrically coupling the antenna assembly to recharging circuitry (block 330). Electrically coupling the antenna assembly to recharging circuitry may include coupling each of the first coil winding, the second coil winding, and the third coil winding to individual diodes configured to rectify the current induced, respectively, in each of the coils. The recharging circuitry may be configured to sum any current or current induced into any of the first coil winding, the second coil winding, and/or the third coil winding to generate a recharging current. In various examples, the antenna assembly is not orientation specific with respect to a direction of the magnetic field that may be imposed onto the antenna assembly of the purpose of generating the recharging current in the antenna assembly. Because the axis of orientation of each of the windings of the coils of the multi-axis antenna are orthogonal to each other, the multi-axis antenna may be configured to produce a level of recharging current that is at least a minimum level of current that could be provided by any of the coils under a maximum coupling efficiency for that coil, the multi-axis antenna configured to provide the minimum level of current regardless of the orientation of a magnetic field imposed on the antenna assembly relative to the orientation of the antenna assembly.

Method 320 includes positioning the antenna assembly within a housing of the implantable medical device (block 332). In various examples, the antenna assembly is positioned within the housing so that an antenna window portion of the housing encircles, (e.g., at least partially surrounds), the antenna assembly. In some examples, the antenna window is made from a material, such as sapphire, that is highly radio frequency transmissive. In some examples, the antenna window is made from a material that is a different material used to form a first housing portion and/or a second housing portion of the housing of the implantable medical device. In various examples the antenna window is formed of a material that allows magnetic fields having frequencies in a range of 10 kHz to 100 MHz to be transmitted through the antenna window for outside the housing of the implantable medical device and be imposed onto the antenna assembly positioned within the housing with no or a very little level of attenuating of the strength of the magnetic field.

Although the examples of a multi-axis antenna have generally been described in this disclosure as having three individual coils, examples of a multi-axis antenna that may be incorporated into an implanted device are not necessarily limited to antenna comprising three coils. A multi-axis antenna may include an antenna that is made from two coils forming parallel connected coils arrange in such a way to provide an efficient level of inductive coupling for certain orientations of the direction of an imposed magnetic field directed toward the device including the two-coil antenna, such as a window 42 of device 30 as illustrated and described with respect to FIG. 2. A multi-axis antenna may also be formed using one or more serially connected or continuously wound coils that forms a curved coil arranged inside curvature of window of a device, such as window 42 of device 30 as shown and described with respect to FIG. 2.

Further, use of the devices, systems, and techniques described in this disclosure are not limited to use in devices only during recharging sessions applied to the devices. An example of a multi-axis antenna as described throughout this disclosure, or any equivalent thereof, may be included a part of a passive device. In some examples, the passive device may not include an internal power source capable of storing electrical energy, and may only operate when energized from an external power source, for example by receiving power from an external device through inductively coupled electrical energy provided by the external device. When operating a passive device, an external device that may include a transmit coil arranged to be electrically energized to generate a magnetic field that is imposed on the multi-axis antenna of the passive device. The imposed magnetic field generates one or more currents in the multi-axis antenna of the passive device, and additional circuitry of the passive device is arranged to receive these induced currents to electrically power and operate the passive device. These current(s) inducted into the multi-axis antenna may be referred to as "operating current" because they are used to electrically power and operate the passive implantable medical device.

Once powered by the induced currents, the implanted medical device may perform a variety of functions, including sensing physiological parameter associated with a patient in order to monitoring and/or diagnose a condition of the patient, and/or to provide therapy, such as electrical stimulation therapy, to the patient while the passive device is being powered through the imposed magnetic field. The need to operate the passive device in some instances may only require that the device be powered for a short interval of time, for example for a thirty-minute time period and only periodically, for example once daily, or in other examples one time per week or once monthly. By eliminating the need to have a power source located within or as part of the passive device, the overall size and/or the dimension of the passive device may be reduced relative to a similar device that includes a power source included as part of the device. The smaller size for the passive device may allow a less intrusive implantation to implant the passive device at the implantation site, and may contribute to patient comfort following implantation of the device due to the smaller size of the implanted device.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processor circuitry," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A method comprising:
   receiving, at a multi-axis antenna of a medical device internal to a patient, a magnetic field having a magnetic field direction, the magnetic field generated by at least one recharging coil, wherein the magnetic field induces one or more electrical currents in one or more of a plurality of coils forming the multi-axis antenna, the plurality of coils comprising a first coil having a first coil axis of orientation, a second coil having a second coil axis of orientation, and a third coil having a third coil axis of orientation;
   rectifying the one or more electrical currents induced in the one or more plurality of coils;
   summing the one or more rectified electrical currents to form a recharging current;
   applying the recharging current to a power source of the medical device to recharge the power source; and switching, with a switching device, the summed one or more electrical currents between the power source and a shunt device, the shunt device comprising an electrically resistive load.

2. The method of claim 1, further comprising matching, with one or more capacitors coupled in parallel with the one or more of the plurality of coils, a frequency of the magnetic field generated by the at least one recharging coil with a resonant frequency of a tank circuit formed by the one or more capacitors coupled in parallel with the one or more of the plurality of coils.

3. The method of claim 1, further comprising preventing, with one or more diodes coupled to the one or more of the plurality of coils, the one or more electrical currents induced in the one or more plurality of coils from being backward driven into another of the plurality of coils.

4. The method of claim 1, further comprising sensing, with sensing circuitry, each of the one or more electrical currents induced in the one or more plurality of coils.

5. The method of claim 1, wherein each of the first coil, the second coil, and the third coil encircle a portion of a ferrite core, and wherein the third coil encircles at least a portion of the first coil and the second coil, and wherein the second coil encircles at least a portion of the first coil.

6. The method of claim 1, further comprising:
determining that the summed one or more electrical currents induced into the plurality of coils is not to be applied to the power source; and
responsive to determining the summed one or more electrical currents is not to be applied to the power source, shunting, with the shunt device coupled in parallel with the power source, the summed one or more electrical currents.

7. The method of claim 1, wherein the medical device is implanted within the patient.

8. The method of claim 1, wherein the first axis, the second axis, and the third axis are orthogonal.

9. A medical device configured to be within a patient, the medical device comprising:
a rechargeable power source configured to provide electrical power to the medical device;
a multi-axis antenna comprising a plurality of coils encircling a ferrite core, the multi-axis antenna configured to generate a recharging current from one or more electrical currents induced into one or more of the plurality of coils when an externally generated magnetic field having a magnetic field direction is imposed onto the multi-axis antenna,
wherein the plurality of coils comprises a first coil having a first coil axis of orientation and formed from first electrically conductive winding, a second coil having a second coil axis of orientation and formed from a second electrically conductive winding, and a third coil having a third coil axis of orientation and formed from a third electrically conductive winding;
one or more diodes coupled to one or more of the plurality of coils and configured to prevent the one or more electrical currents induced into the one or more of the plurality of coils from being backward driven into another of the one or more of the plurality of coils;
recharging circuitry coupled to the multi-axis antenna and to the rechargeable power source, the recharging circuitry configured to direct a sum of the one or more electrical currents induced in one or more of the plurality of coils into the rechargeable power source; and a switching device, coupled to the recharging circuitry and the multi-axis antenna, the switching device configured to switch the sum of the one or more electrical currents between the rechargeable power source and a shunt device, the shunt device comprising an electrically resistive load.

10. The medical device of claim 9, further comprising one or more capacitors coupled in parallel with the one or more of the plurality of coils to match a frequency of the magnetic field generated externally with a resonant frequency of a tank circuit formed by the one or more capacitors coupled in parallel with the one or more of the plurality of coils.

11. The medical device of claim 9, wherein the one or more diodes are configured to rectify the one or more electrical currents induced in the one or more plurality of coils.

12. The medical device of claim 9, further comprising sensing circuitry coupled to the recharging circuitry and the multi-axis antenna that senses the one or more electrical currents induced in the one or more plurality of coils.

13. The medical device of claim 9, wherein each of the first coil, the second coil, and the third coil encircle a portion of the ferrite core, and wherein the third coil encircles at least a portion of the first coil and the second coil, and wherein the second coil encircles at least a portion of the first coil.

14. The medical device of claim 9, wherein the first axis, the second axis, and the third axis are orthogonal.

15. A recharging system for recharging a rechargeable power source located in a medical device internal to a patient, the recharging system comprising:
an electrical power source;
at least one recharging coil coupled to the electrical power source and configured to generate a magnetic field having a magnetic field direction and frequency when electrically energized by the electrical power source;
a multi-axis antenna located in the medical device, the multi-axis antenna comprising a plurality of coils configured to generate a recharging current when the magnetic field generated by the at least one recharging coil is imposed onto the multi-axis antenna,
wherein the plurality of coils comprises a first coil having a first coil axis of orientation, a second coil having a second coil axis of orientation, and a third coil having a third coil axis of orientation;
one or more capacitors coupled in parallel with one or more of the plurality of coils, where the one or more capacitors are configured to have a resonant frequency that matches the magnetic field frequency applied by the at least one recharging coil;
a common node to the plurality of coils, the common node configured to sum one or more currents induced into one or more of the first coil, the second coil, and the third coil to generate the recharging current; and
a switching device coupled to the multi-axis antenna, the rechargeable power source of the medical device, and a shunt device, the switching device configured to be controlled by recharging circuitry to couple the recharging current to the rechargeable power source to recharge the electrical energy stored in the rechargeable power source, or to couple the recharging current to the shunt device, and the shunt device comprising an electrically resistive load.

16. The system of claim 15, further comprising one or more diodes coupled to one or more of the plurality of coils, the one or more diodes configured to rectify the one or more currents induced in the one or more plurality of coils.

17. The system of claim 15, further comprising sensing circuitry coupled to the recharging circuitry and the multi-axis antenna that senses the one or more currents induced in the one or more plurality of coils.

* * * * *